United States Patent
McGall et al.

(10) Patent No.: US 6,410,675 B2
(45) Date of Patent: Jun. 25, 2002

(54) FUNCTIONALIZED SILICON COMPOUNDS AND METHODS FOR THEIR SYNTHESIS AND USE

(75) Inventors: Glenn McGall, Mountain View; Jonathan Eric Forman, San Jose, both of CA (US)

(73) Assignee: Affymetrix, Inc., Santa Clara, CA (US)

( * ) Notice: Subject to any disclaimer, the term of this patent is extended or adjusted under 35 U.S.C. 154(b) by 0 days.

(21) Appl. No.: 09/832,490

(22) Filed: Apr. 11, 2001

Related U.S. Application Data

(60) Division of application No. 09/418,044, filed on Oct. 13, 1999, which is a continuation-in-part of application No. 09/172,190, filed on Oct. 13, 1998, now Pat. No. 6,262,216.

(51) Int. Cl.[7] .................. C08G 77/00; C08G 77/04; C12Q 1/68; C07H 19/00; G01N 15/06
(52) U.S. Cl. ................ 528/10; 528/25; 528/28; 528/33; 435/6; 536/22.1; 536/23.1; 536/24.3; 536/25.3; 536/25.33; 422/68.1; 422/50
(58) Field of Search .............. 435/6; 536/22.1, 536/23.1, 24.3, 24.33, 25.3; 528/10, 25, 28, 33; 422/68.1, 50

(56) References Cited

U.S. PATENT DOCUMENTS

| 3,285,886 A | 11/1966 | Gunderson et al. ........ 260/80.3 |
| 4,448,694 A | 5/1984 | Plueddemann .............. 210/682 |
| 4,526,996 A | 7/1985 | Kilgour et al. ............. 556/413 |

(List continued on next page.)

FOREIGN PATENT DOCUMENTS

| CA | 1238997 | 7/1988 | ........... C08L/83/06 |
| DE | 2144759 | 3/1972 | ............ G03C/5/55 |
| DE | 2821016 | 11/1978 | ............ C09D/5/10 |
| DE | 3500576 | 7/1985 | ............ G03C/1/71 |
| EP | 0011782 | 6/1980 | ........... C08L/57/04 |
| EP | 0136880 | 4/1985 | ............ C07F/7/18 |
| EP | 0368279 | 5/1990 | ............ C07F/7/18 |
| EP | 0862068 | 9/1998 | ............ G02B/1/04 |
| JP | 60-169847 | 9/1985 | ............ G03C/1/00 |

(List continued on next page.)

OTHER PUBLICATIONS

Arkles, B., "Tailoring surfaces with silanes", *Chemtech*, pp. 766–778, (Dec. 1977).

Barber, H.J., "Some Sulphonyl Derivatives of Amidines and Imino-ethers", *Journal of the Chemical Society*, pp. 101–104, (Mar. 1943).

(List continued on next page.)

*Primary Examiner*—Jezia Riley
(74) *Attorney, Agent, or Firm*—Schwegman, Lundberg, Woessner & Kluth, P.A.

(57) ABSTRACT

Provided are functionalized silicon compounds and methods for their synthesis and use. The functionalized silicon compounds include at least one activated silicon group and at least one derivatizable functional group. Exemplary derivatizable functional groups include hydroxyl, amino, carboxyl and thiol, as well as modified forms thereof, such as activated or protected forms. The functionalized silicon compounds may be covalently attached to surfaces to form functionalized surfaces which may be used in a wide range of different applications. In one embodiment, the silicon compounds are attached to the surface of a substrate comprising silica, such as a glass substrate, to provide a functionalized surface on the substrate, to which molecules, including polypeptides and nucleic acids, may be attached. In one embodiment, after covalent attachment of a functionalized silicon compound to the surface of a solid silica substrate to form a functionalized coating on the substrate, an array of nucleic acids may be covalently attached to the substrate. Thus, the method permits the formation of high density arrays of nucleic acids immobilized on a substrate, which may be used, for example, in conducting high volume nucleic acid hybridization assays.

9 Claims, 31 Drawing Sheets

VI          Formula 6a

VII

U.S. PATENT DOCUMENTS

| | | | |
|---|---|---|---|
| 4,990,641 A | | 2/1991 | Kabeta .................... 556/419 |
| 5,013,771 A | | 5/1991 | Guillet et al. ............... 523/202 |
| 5,143,854 A | | 9/1992 | Pirrung et al. .............. 436/518 |
| 5,200,051 A | | 4/1993 | Cozzette et al. ............ 204/403 |
| 5,206,285 A | * | 4/1993 | Castellucci et al. ......... 524/588 |
| 5,252,743 A | | 10/1993 | Barrett et al. ............ 548/303.7 |
| 5,324,591 A | | 6/1994 | Georger, Jr. et al. ........ 428/552 |
| 5,324,633 A | | 6/1994 | Fodor et al. .................... 435/6 |
| 5,384,261 A | | 1/1995 | Winkler et al. ............. 436/518 |
| 5,393,535 A | | 2/1995 | Bishop ....................... 148/253 |
| 5,405,783 A | | 4/1995 | Pirrung et al. .............. 436/518 |
| 5,412,087 A | | 5/1995 | McGall et al. ............. 536/24.3 |
| 5,424,186 A | | 6/1995 | Fodor et al. .................... 435/6 |
| 5,445,934 A | | 8/1995 | Fodor et al. .................... 435/6 |
| 5,451,683 A | | 9/1995 | Barrett et al. ............ 548/302.7 |
| 5,510,270 A | | 4/1996 | Fodor et al. ................. 435/518 |
| 5,527,681 A | | 6/1996 | Holmes ......................... 435/6 |
| 5,545,531 A | | 8/1996 | Rava et al. ..................... 435/6 |
| 5,547,839 A | | 8/1996 | Dower et al. .................. 435/6 |
| 5,571,639 A | | 11/1996 | Hubbell et al. ................ 430/5 |
| 5,578,832 A | | 11/1996 | Trulson et al. ........... 250/458.1 |
| 5,599,695 A | | 2/1997 | Pease et al. ............... 435/91.1 |
| 5,624,711 A | | 4/1997 | Sundberg et al. ........... 427/261 |
| 5,631,734 A | | 5/1997 | Stern et al. ................. 356/317 |
| 5,677,195 A | | 10/1997 | Winkler et al. ............. 436/518 |
| 5,700,637 A | | 12/1997 | Southern ....................... 435/6 |
| 5,710,000 A | | 1/1998 | Sapolsky et al. ............... 435/6 |
| 5,744,101 A | | 4/1998 | Fodor et al. ................. 422/131 |
| 5,744,305 A | | 4/1998 | Fodor et al. .................... 435/6 |
| 5,779,904 A | * | 7/1998 | Ruderman et al. ..... 210/500.25 |
| 6,262,216 B1 | | 7/2001 | McGall ....................... 528/10 |

FOREIGN PATENT DOCUMENTS

| | | | |
|---|---|---|---|
| JP | 5004994 | 1/1993 | ............. C07F/7/18 |
| JP | 5-320517 | 12/1993 | ........... C08L/83/08 |
| JP | 7-102167 | 4/1995 | ........... C08L/71/02 |
| JP | 7-157971 | 6/1995 | ........ D06M/13/513 |
| JP | 7-310006 | 11/1995 | ........... C08L/71/02 |
| JP | 7-331014 | 12/1995 | ........... C08L/33/00 |
| WO | 89/10977 | 11/1989 | ............ C12Q/1/68 |
| WO | 92/10092 | 6/1992 | ............ A01N/1/02 |
| WO | WO-9515740 A1 * | 6/1995 | |
| WO | 97/10365 | 3/1997 | ............ C12Q/1/68 |
| WO | 97/39151 | 10/1997 | ............ C12Q/1/68 |
| WO | 98/11092 | 3/1998 | ......... C07D/401/04 |

OTHER PUBLICATIONS

Barbot, F., "N–Tosy Iminoethers et Iminocarbonates D'Alkyle : Synthons D'Amines Phimaires—A Structure Ramifiee", *Tetrahedron Letters*, 30 (2), pp. 185–186, (1989).

Beckwith, A.L., et al., "Cyclization of 3–Allylhex05–enyl Radical: Mechanism, and Implications concerning the Structures of Cyclopolymers", *Journal of the Chemical Society Perkin Transactions II*, pp. 1726–1733, (1975).

Bos, J.L., et al., "Amino–acid substitutions at codon 13 of the N–ras oncogene in human acute myeloid leukaemia", *Nature*, 315, pp. 726–730, (Jun. 27, 1985).

Bubnov, Y.N., et al., "Synthesis of compounds of the triallylmethane series based on reactions of triallylborane and derivatives of carbonic acid", *Russian Chemical Bulletin*, 45 (11), pp. 2598–2601, (Nov. 1996).

Chee, M., et al., "Accessing Genetic Information with High–Density DNA Arrays", *Science*, 274, pp. 610–614, (Oct. 25, 1996).

Chujo, Y., et al., "Synthesis of Triethoxysilyl–Terminated Polyoxazolines and Their Cohydrolysis Polymerization with Tetraethoxysilane", *Macromolecules*, 26 (21), pp. 5681–5686, (1993).

Curran, D.P., et al., "The Tin Hydride Reductive Decyanation of Geminal Dinitriles", *Synlett*, No. 2, pp. 107–108, (Feb. 1991).

de Saizieu, A., et al., "Bacterial transcript imaging by hybridization of total RNA to oligonucleotide arrays", *Nature Biotechnology*, 16, pp. 45–48, (Jan. 1998).

Dreyfuss, M.P., "A Convenient Method for Utilizing the Allyl Grignard Reagent", *The Journal of Organic Chemistry*, 28 (11), pp. 3269–3272, (Nov. 1963).

Elder, J.K., "Analysis of DNA oligonucleotide hybridization data by maximum entropy", In: Maximum Entropy and Bayesian Methods—Proceedings of the Twelfth International Workshop, Mohammad–Dhafari and Demoment, G., Eds., Kluwer Academic Publishers, Paris, France, pp. 363–371, (1993).

Hochgeschwender, et al., "Preferential Expression of a Defined T–cell Receptor Beta–chain gene in Hapten–specific Cytotoxic T–cell Clones", *Nature*, 322, pp. 376–378, (1986).

Hong, S.G., et al., "Investigation of primers reducing the pink–ring formation in multilayer printed curcuit boards", *Die Angewandte Makromolekulare Chemie*, 231 (4043), pp. 91–108, (1995).

Kabeta, K., "Preparation of N,N–bis(alkoxysilylpropyl)amino=hyrdocarbylamines", *Chemical Abstracts*, 113, Abstract No. 41014c, pp. 41018, (1990).

Kirkland, J.J., et al., "Synthesis and Characterization of Highly Stable Bonded Phases for High–Performance Liquid Chromatography Column Packings", *Anal. Chem.*, 61, pp. 2–11, (1989).

Lockhart, D.J., et al., "Expression monitoring by hybridization to high–density oligonucleotide arrays", *Nature Biotechnology*, 14 (13), pp. 1675–1680, (Dec. 1996).

McGall, G., et al., "Light–Directed synthesis of high–density oligonucleotide arrays using semiconductor photoresists", *PNAS*, 93, pp. 13555–13560, (Nov. 1996).

McGall, G.H., et al., "The Efficiency of Light–Directed Synthesis of DNA Arrays on Glass Substrates", *Journal of the American Chemical Society*, 119 (22), pp. 5081–5090, (Jun. 4, 1997).

Pease, A.C., et al., "Light–generated oligonucleotide arrays for rapid DNA sequence analysis", *PNAS*, 91, pp. 5022–5026, (May 1994).

Reeve, W., et al., "Synthesis of Tetraallylmethane", *The Journal of Organic Chemistry*, 34 (6), pp. 1921–1923, (Jun. 1969).

Schneider, P., et al., "Tailor–Made Silylating Agents for Efficient Surface Modification", *Synthesis*, pp. 1027–1031, (Nov. 1990).

Southern, et al., "Analyzing and comparing nucleic acid sequences by hybridization to arrays of oligonuceotides: evaluation using experimental models", *Genomics*, 13, pp. 1008–1017, (1992).

Verlaan–de Vries, et al., "A dot–blot screening procedure for mutated ras oncogenes using synthetic oligodeoxynucleotides", *Gene*, 50, pp. 313–320, (1986).

* cited by examiner

VI

Formula 6a

VII

VIII

Formula 10

Formula 11

Formula 16a          Formula 16b

Formula 14

Formula 15

Formula 17

Formula 18

Formula 19

Formula 20

Formula 21

XXIII

XXV

XXVI

XXXIIIa  XXXIa  XXXIIa

XXXIIIb  XXXIb  XXXIIb

FUNCTIONALIZED SILICON COMPOUNDS AND METHODS FOR THEIR SYNTHESIS AND USE

CROSS REFERENCE TO RELATED APPLICATIONS

This application is a divisional of U.S. patent application Ser. No. 09/418,044, filed Oct. 13, 1999, which application is a Continuation-in-Part of U.S. patent application Ser. No. 09/172,190, filed Oct. 13, 1998, issued as U.S. Pat. No. 6,262,216 on Jul. 17, 2001, both of which applications are incorporated in their entirety by reference.

TECHNICAL FIELD

This application relates to silicon compounds, methods of making silicon compounds, and methods for use of silicon compounds as silylating agents in the treatment of surfaces, such as glass.

BACKGROUND ART

Silylating agents have been developed in the art which react with and coat surfaces, such as silica surfaces. For example, silylating agents for use in modifying silica used in high performance chromatography packings have been developed. Monofunctional silylating agents have been used to form monolayer surface coatings, while di- and tri-functional silylating agents have been used to form polymerized coatings on silica surfaces. Many silylating agents, however, produce coatings with undesirable properties including instability to hydrolysis and the inadequate ability to mask the silica surface which may contain residual acidic silanols.

Silylating agents have been developed for the silylation of solid substrates, such as glass substrates, that include functional groups that may be derivatized by further covalent reaction. The silylating agents have been immobilized on the surface of substrates, such as glass, and used to prepare high density immobilized oligonucleotide probe arrays. For example, N-(3-(triethoxysilyl)-propyl)-4-hydroxybutyramide (PCR Inc., Gainesville, Fla. and Gelest, Tullytown, Pa.) has been used to silylate a glass substrate prior to photochemical synthesis of arrays of oligonucleotides on the substrate, as described in McGall et al., *J. Am. Chem. Soc.*, 119:5081–5090 (1997), the disclosure of which is incorporated herein by reference.

Hydroxyalkylsilyl compounds that have been used to prepare hydroxyalkylated substances, such as glass substrates. N,N-bis(hydroxyethyl) aminopropyl-triethoxysilane has been used to treat glass substrates to permit the synthesis of high-density oligonucleotide arrays. McGall et al., *Proc. Natl. Acad. Sci.*, 93:13555–13560 (1996); and Pease et al., *Proc. Natl. Acad. Sci.*, 91:5022–5026 (1994), the disclosures of which are incorporated herein. Acetoxypropyl-triethoxysilane has been used to treat glass substrates to prepare them for oligonucleotide array synthesis, as described in PCT WO 97/39151, the disclosure of which is incorporated herein. 3-Glycidoxy propyltrimethoxysilane has been used to treat a glass support to provide a linker for the synthesis of oligonucleotides. EP Patent Application No. 89 120696.3.

Methods have been developed in the art for stabilizing surface bonded silicon compounds. The use of sterically hindered silylating agents is described in Kirkland et al., *Anal. Chem.* 61:2–11 (1989); and Schneider et al., *Synthesis*, 1027–1031 (1990). However, the use of these surface bonded silylating agents is disadvantageous, because they typically require very forcing conditions to achieve bonding to the glass, since their hindered nature makes them less reactive with the substrate.

It is an object of the invention to provide functionalized silicon compounds that are provided with derivatizable functional groups, that can be used to form functionalized coatings on materials, such as glass. It is a further object of the invention to provide functionalized silicon compounds that can be used to form coatings on materials that are stable under the conditions of use.

DISCLOSURE OF THE INVENTION

Provided are functionalized silicon compounds and methods for their use. The functionalized silicon compounds include an activated silicon group and a derivatizable functional group. Exemplary derivatizable functional groups include hydroxyl, amino, carboxyl and thiol, as well as modified forms thereof, such as activated or protected forms. The functionalized silicon compounds may be covalently attached to surfaces to form functionalized surfaces which may be used in a wide range of different applications. In one embodiment, the silicon compounds are attached to the surface of a substrate comprising silica, such as a glass substrate, to provide a functionalized surface on the silica containing substrate, to which molecules, including polypeptides and nucleic acids, may be attached. In one preferred embodiment, after covalent attachment of a functionalized silicon compound to the surface of a solid silica substrate to form a functionalized coating on the substrate, an array of nucleic acids may be covalently attached to the substrate. Thus, the method permits the formation of high density arrays of nucleic acids immobilized on a substrate, which may be used in conducting high volume nucleic acid hybridization assays.

BRIEF DESCRIPTION OF THE DRAWINGS

FIG. 1 shows the structure of the functionalized silicon compounds VI and VII and compounds of Formula 6a.

MODES FOR CARRYING OUT THE INVENTION

Figure 1:
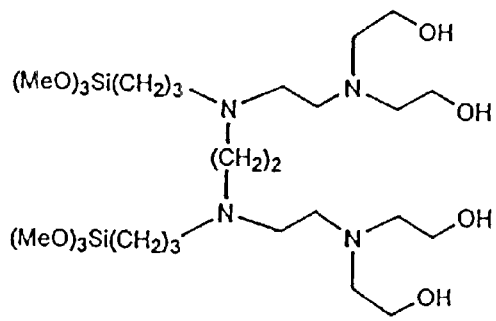
Figure 1:
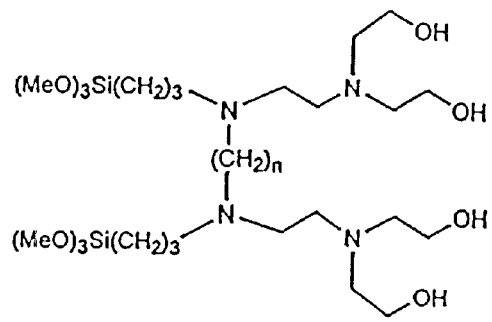
Figure 1:
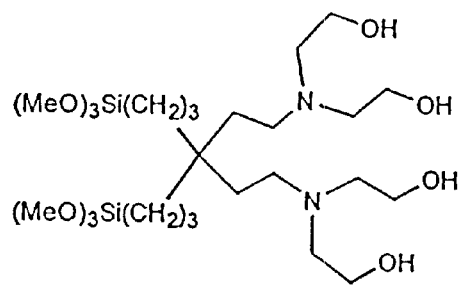

Functionalized silicon compounds are provided, as well as methods for their synthesis and use. The functionalized silicon compounds may be used to form functionalized coatings on a variety of surfaces such as the surfaces of glass substrates.

Functionalized Silicon Compounds

A variety of functionalized silicon compounds, which are available commercially, or which may be synthesized as disclosed herein, may be used in the methods disclosed herein to react with surfaces to form functionalized surfaces which may be used in a wide range of different applications. In one embodiment, the functionalized silicon compounds are covalently attached to surfaces to produce functionalized surfaces on substrates. For example, the silicon compounds may be attached to the surfaces of glass substrates, to provide a functionalized surface to which molecules, including polypeptides and nucleic acids, may be attached.

As used herein, the term "silicon compound" refers to a compound comprising a silicon atom. In a preferred embodiment, the silicon compound is a silylating agent comprising an activated silicon group, wherein the activated silicon group comprises a silicon atom covalently linked to at least one reactive group, such as an alkoxy or halide, such that the silicon group is capable of reacting with a functional group, for example on a surface of a substrate, to form a covalent bond with the surface. For example, the activated silicon group on the silicon compound can react with the surface of a silica substrate comprising surface Si—OH groups to create siloxane bonds between the silicon compound and the silica substrate. Exemplary activated silicon groups include —Si(OMe)$_3$; —SiMe(OMe)$_2$; —SiMeCl$_2$; SiMe(OEt)$_2$; SiCl$_3$ and —Si(OEt)$_3$.

As used herein, the term "functionalized silicon compound" refers to a silicon compound comprising a silicon atom and a derivatizable functional group. In a preferred embodiment, the functionalized silicon compound is a functionalized silylating agent and includes an activated silicon group and a derivatizable functional group. As used herein, the term "derivatizable functional group" refers to a functional group that is capable of reacting to permit the formation of a covalent bond between the silicon compound and another substance, such as a polymer. Exemplary derivatizable functional groups include hydroxyl, amino, carboxy, thiol, and amide, as well as modified forms thereof, such as activated or protected forms. Derivatizable functional groups also include substitutable leaving groups such as halo or sulfonate. In one preferred embodiment, the derivatizable functional group is a group, such as a hydroxyl group, that is capable of reacting with activated nucleotides to permit nucleic acid synthesis. For example, the functionalized silicon compound may be covalently attached to the surface of a substrate, such as glass, and then derivatizable hydroxyl groups on the silicon compound may be reacted with an activated phosphate group on a protected nucleotide phosphoramidite or H-phosphonate, and then stepwise addition of further protected nucleotide phosphoramidites or H-phosphonates can result in the formation of a nucleic acid covalently attached to the support. The nucleic acids also may be attached to the derivatizable group via a linker. In a further embodiment, arrays of nucleic acids may be formed covalently attached to the substrate which are useful in conducting nucleic acid hybridization assays.

The term "polynucleotide" or "nucleic acid" as used herein refers to a polymeric form of nucleotides of any length, either ribonucleotides or deoxyribonucleotides, that comprise purine and pyrimidine bases, or other natural, chemically or biochemically modified, non-natural, or derivatized nucleotide bases. The backbone of the polynucleotide can comprise sugars and phosphate groups, as may typically be found in RNA or DNA, or modified or substituted sugar or phosphate groups. A polynucleotide may comprise modified nucleotides, such as methylated nucleotides and nucleotide analogs. The sequence of nucleotides may be interrupted by non-nucleotide components.

The functionalized silicon compounds used to form coatings on a surface may be selected, and obtained commercially, or made synthetically, depending on their properties under the conditions of intended use. For example, functionalized silicon compounds may be selected for silanization of a substrate that are stable after the silylation reaction to hydrolysis.

For example, in one embodiment, the functionalized silicon compounds are used to form a coating on a solid substrate, and include functional groups that permit the covalent attachment or synthesis of nucleic acid arrays to the solid substrate, such as glass. The resulting substrates are useful in nucleic acid hybridization assays, which are conducted, for example in aqueous buffers. In one embodiment, preferred are silicon compounds that produce coatings that are substantially stable to hybridization assay conditions, such as phosphate or TRIS buffer at about pH 6–9, and at elevated temperatures, for example, about 25–65° C., for about 1 to 72 hours, such that hydrolysis is less than about 90%, e.g., less than about 50%, or e.g, less than about 20%, or about 10%. The functionalized surfaces on the substrate, formed by covalent attachment of functionalized silicon compounds, advantageously are substantially stable to provide a support for biomolecule array synthesis and to be used under rigorous assay conditions, such as nucleic acid hybridization assay conditions.

The functionalized silicon compound in one embodiment includes at least one activated silicon group and at least one derivatizable functional group. In one embodiment, the functionalized silicon compound includes at least one activated silicon group and a plurality of derivatizable functional groups, for example, 2, 3, 4 or more derivatizable functional groups. In another embodiment, the functionalized silicon compound includes at least one derivatizable functional group and a plurality of activated silicon groups, for example, 2, 3, 4 or more activated silicon groups. Methods of making the functionalized silicon compounds are provided as disclosed herein, as well as methods of use of the functionalized silicon compounds, including covalent attachment of the silicon compounds to surfaces of substrates to form functionalized surfaces, and further derivation of the surfaces to provide arrays of nucleic acids for use in assays on the surfaces.

In one embodiment, there is provided a method of functionalizing a surface, the method comprising covalently attaching to the surface a functionalized silicon compound, wherein the functionalized silicon compound comprises at least one derivatizable functional group and a plurality of activated silicon groups, for example, 2, 3, 4 or more activated silicon groups. The method may further comprise covalently attaching a plurality of functionalized silicon compounds to the surface, and forming an array of nucleic acids covalently attached to the functionalized silicon compounds on the surface.

Exemplary functionalized silicon compounds include compounds of Formula 1 shown below:

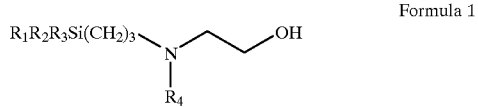

Formula 1 wherein $R_1$ and $R_2$ are independently a reactive group, such as halide or alkoxy, for example —$OCH_3$ or —$OCH_2CH_3$, and $R_3$ is alkoxy, halide or alkyl; and wherein $R_4$ is a hydrophobic and/or sterically hindered group. In the functionalized silylating agents of Formula 1, $R_4$ may be alkyl or haloalkyl, for example, —$CH_3$, —$CH_2CH_3$, —$CH(CH_3)_2$, —$C(CH_3)_3$, or —$CH(CF_3)_2$. A hydrophobic and/or sterically hindered $R_4$ group, such as isopropyl or isobutyl, may be used to increase the hydrolytic stability of the resulting surface layer. Further hydrophobicity may be imparted by the use of a fluorocarbon $R_4$ group, such as hexafluoroisopropyl (($CF_3)_2CH$—).

An exemplary compound of Formula 1 is silicon compound I below:

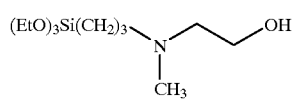

I

In general, silicon compounds provide uniform and reproducible coatings. Silicon compounds with one derivatizable functional group can provide a lower concentration of surface derivatizable functional groups at maximum coverage of the substrate than the silicon compounds including multiple derivatizable functional groups. Silicon compounds with one derivatizable functional group, such as silicon compounds of Formula 1, however, which include a hydrophobic and/or sterically hindered R group, such as isopropyl or isobutyl, are advantageous since the hydrophobic or sterically hindered R group increases the hydrolytic stability of the resulting surface layer.

In one embodiment the functionalized silicon compounds of Formula 2 are provided:

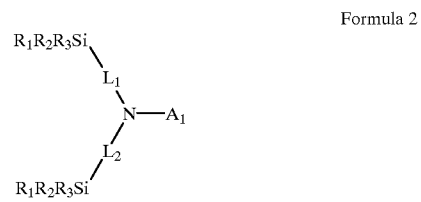

Formula 2

In Formula 2, in one embodiment, $R_1$, $R_2$ and $R_3$ are independently a reactive group, such as alkoxy or halide, for example, —$OCH_3$, or —$OCH_2CH_3$, and wherein, in one embodiment, $R_1$, $R_2$ and $R_3$ are each —$OCH_3$. In one embodiment $R_1$ and $R_2$ are independently a reactive group, such as alkoxy or halide, for example —$OCH_3$ or —$OCH_2CH_3$, and $R_3$ is an alkoxy or halide group or an alkyl group, such as —$CH_3$, or substituted alkyl group.

In Formula 2, in one embodiment, $L_1$ and $L_2$ are independently alkyl, preferably —$(CH_2)_n$—, wherein n=2 to 10, e.g., 3 to 4, or e.g., 2–3.

In Formula 2, in one embodiment, $A_1$ is H or a moiety comprising one or more derivatizable functional groups. In one embodiment, $A_1$ is a moiety comprising an amino group or a hydroxyl group, such as —$CH_2CH_2OH$. In another embodiment, $A_1$ is, for example, a branched hydrocarbon including a plurality of derivatizable functional groups, such as hydroxyl groups. In one embodiment in Formula 2, $A_1$ is:

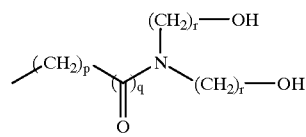

wherein p is 1–10, q is 0 or 1, and r is 2–5.

In one embodiment of Formula 2, $R_1$ and $R_2$ are independently alkoxy or halide; $R_3$ is alkoxy, halide or alkyl; $L_1$ and $L_2$ are both —$(CH_2)_n$—, wherein n=2 to 10, e.g., 2 to 3; and $A_1$ is H or a moiety comprising one or more derivatizable functional groups.

Figure 7:
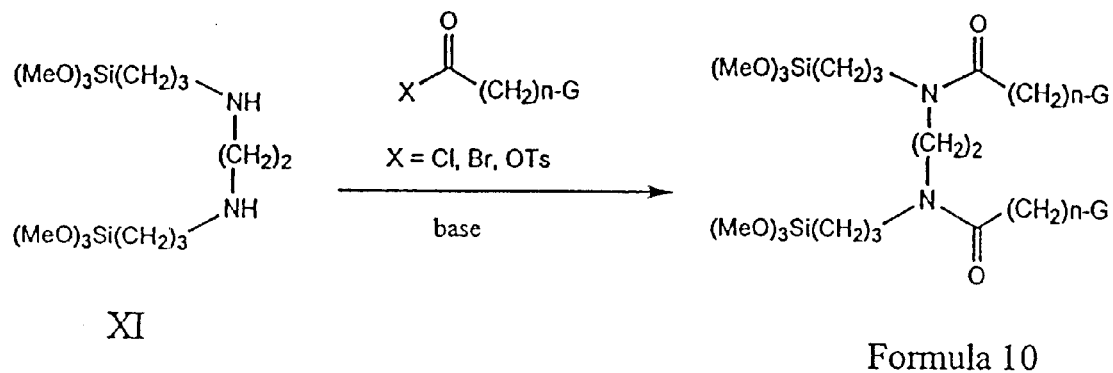
FIG. 7 shows schemes showing the synthesis of compounds of Formula 10 or 11.
Figure 7:
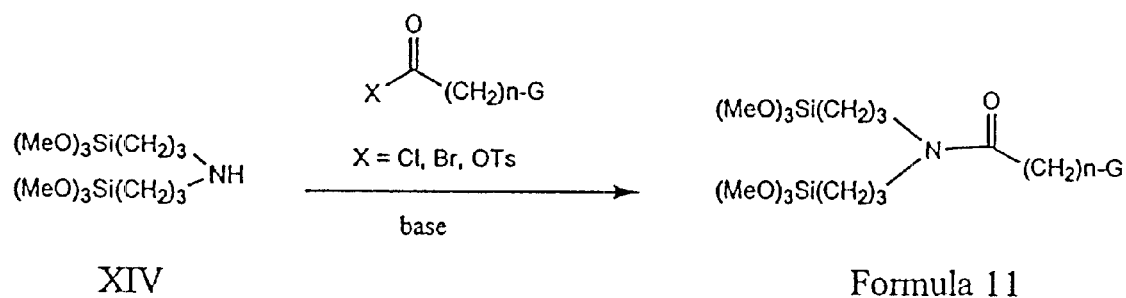

Exemplary compounds of Formula 2 include compounds II, III and IV below. Other silicon compounds of Formula 2 that may be used to form functional surface coatings with enhanced hydrolytic stability include silicon compounds IX and X, shown in FIG. 3. In compound VIII, the triethoxysilyl group is shown by way of example, however alternatively, the activated silicon group may be other activated silicon groups or mixtures thereof, such as trimethoxysilyl. In another embodiment, there is provided a compound of Formula 11, wherein n is, for example, 1 to 10, e.g., 1–3, and G is a derivatizable functional group, such as hydroxyl, protected hydroxyl or halide such as Cl or Br, as shown in FIG. 7.

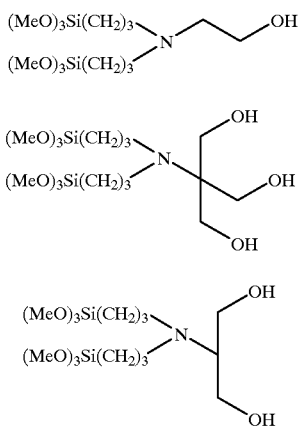

Figure 10:
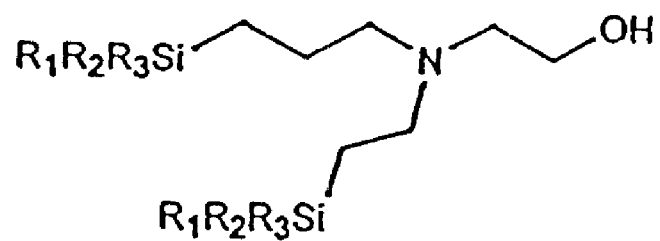
FIG. 10 illustrates the structure of compounds of Formula 14 and 15.
Figure 10:
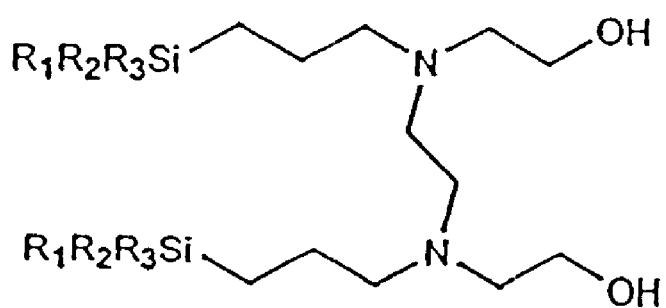

In another embodiment, silicon compounds of Formula 14 in FIG. 10 are provided wherein, $R_1$, $R_2$ are independently a reactive group such as alkoxy, for example —$OCH_3$ or —$OCH_2CH_3$, or halide; and $R_3$ is a reactive group such as alkoxy or halide, or optionally alkyl.

Another embodiment of Formula 2 is as follows:

In one embodiment of Formula 2, $R_1$, $R_2$, $R_3$ are independently a reactive group, such as alkoxy or halide, for example, —$OCH_3$, or —$OCH_2CH_3$, for example, in one embodiment, $R_1$, $R_2$ and $R_3$ are each —$OCH_3$; or in another embodiment, $R_1$ and $R_2$ are independently a reactive group, such as alkoxy or halide, for example —$OCH_3$ or —$OCH_2CH_3$, and $R_3$ is an alkoxy or halide group or an alkyl group, such as —$CH_3$, or substituted alkyl group.

In one embodiment of Formula 2, $L_1$ and $L_2$ are independently alkyl, for example, linear or branched alkyl or heteroalkyl, e.g., C1–C25 alkyl, for example, —$(CH_2)_n$—, wherein n=2 to 10, e.g., 3 to 4, or e.g., 2–3. For example, $L_1$ and $L_2$ may optionally comprise a heteroalkyl comprising a heteroatom such as O, S, or N. Each $L_1$ and $L_2$ independently comprise one or more derivatizable groups, e.g., 1–4 derivatizable groups, such as hydroxyl, amino or amido.

In Formula 2, in one embodiment, $A_1$ is H or a moiety comprising one or more derivatizable functional groups. In one embodiment, $A_1$ is a moiety comprising an amino group or a hydroxyl group, such as —$CH_2CH_2OH$. In another embodiment, $A_1$ is, for example, a linear or branched alkyl or heteroalkyl group including a plurality of derivatizable functional groups, for example, 1, 2, or 3 derivatizable groups. In one embodiment, $A_1$ may comprise a linear or branched alkyl or heteroalkyl, wherein one or more carbon atoms of the alkyl group is functionalized, for example, to comprise an amide.

Figure 13:
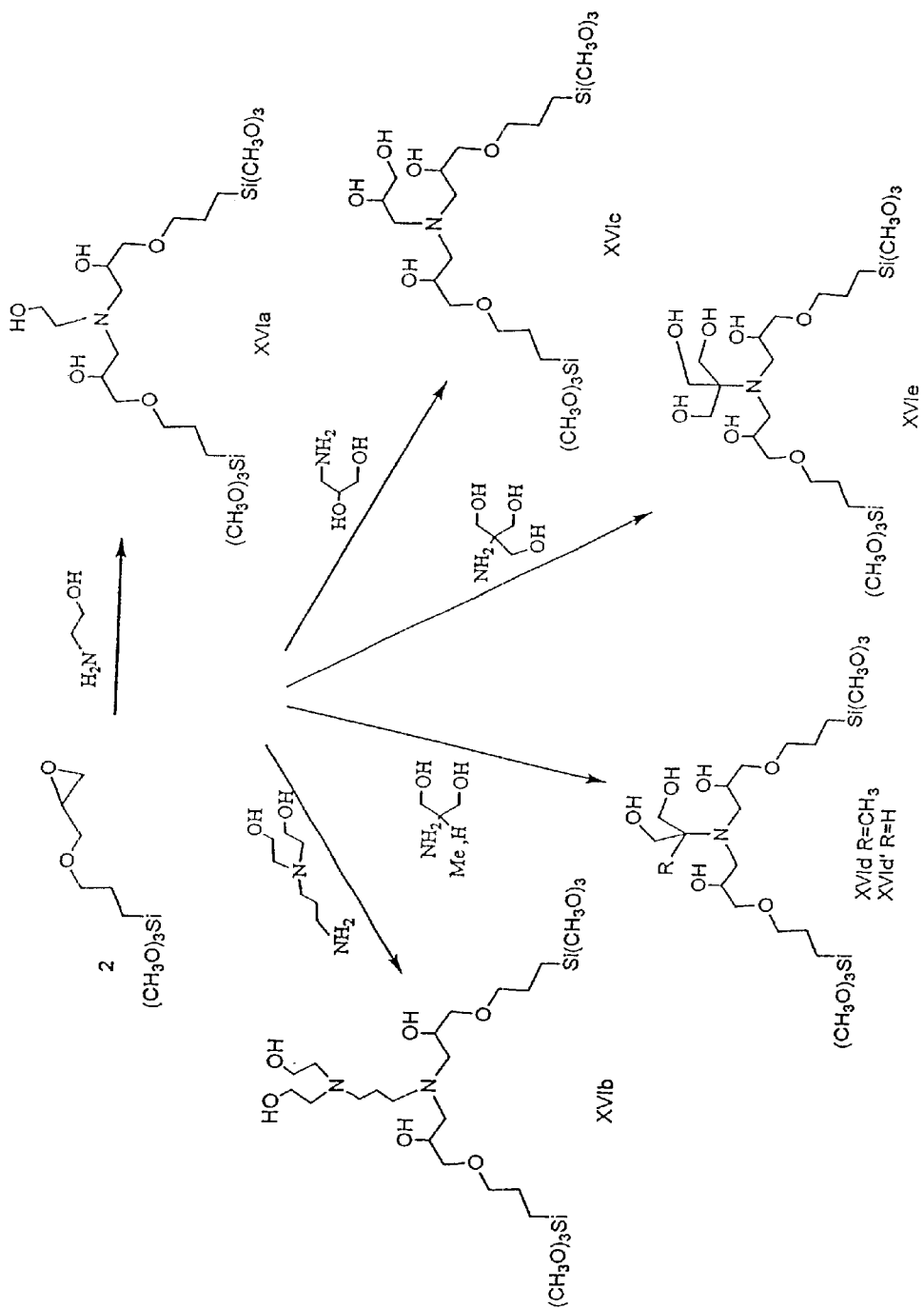
FIG. 13 is a scheme showing the synthesis of silicon compounds XVIa–e.
Figure 14:
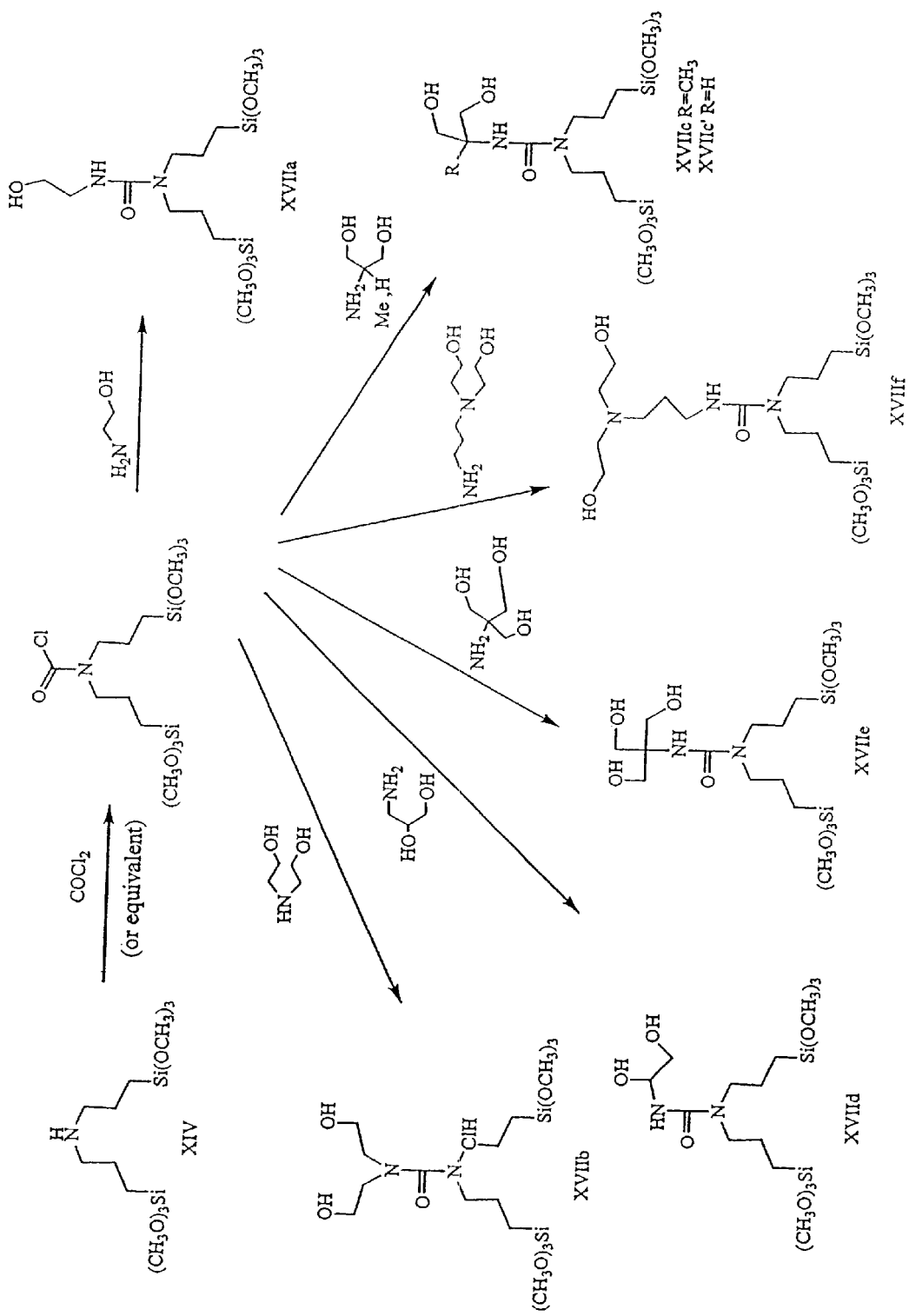
FIG. 14 is a scheme showing the synthesis of silicon compounds XVIIa–f.
Figure 19:
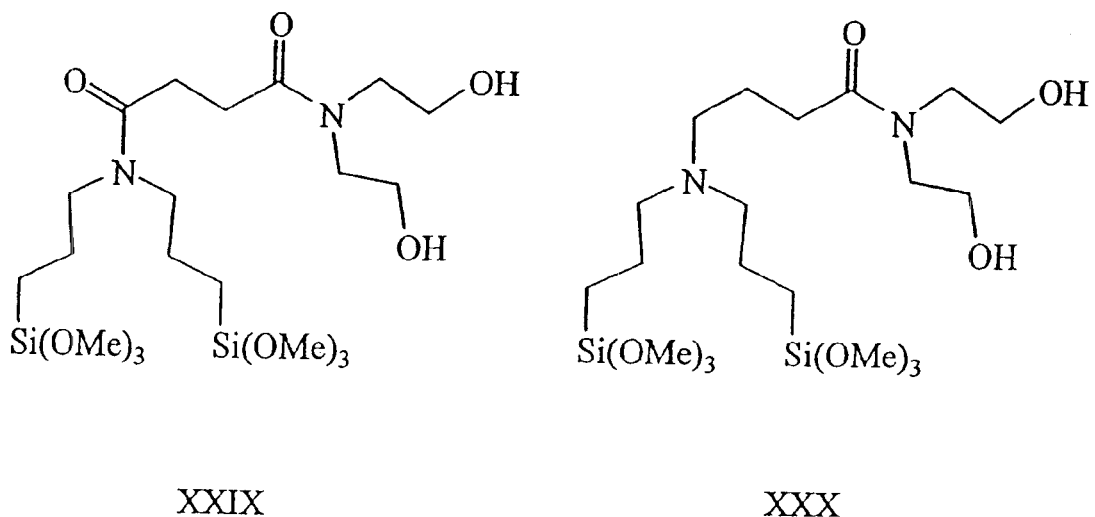
FIG. 19 shows the structure of exemplary silicon compounds XXIX and XXX.

Examples of compounds include compounds XVIa–e shown in FIG. 13, and compounds XVIIIa–f shown in FIG. 14. Other examples include compound XII in FIG. 5 and compound XV in FIG. 6, as well as compounds XXIX and XXX in FIG. 19.

Figure 15:
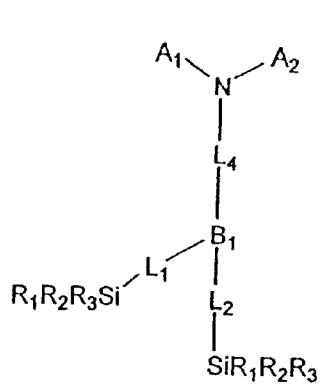
FIG. 15 shows the structure of compounds of the general Formulas 17–21.
Figure 15:
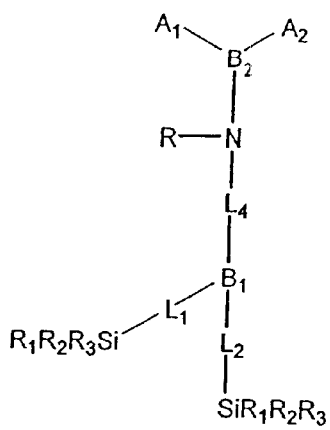
Figure 15:
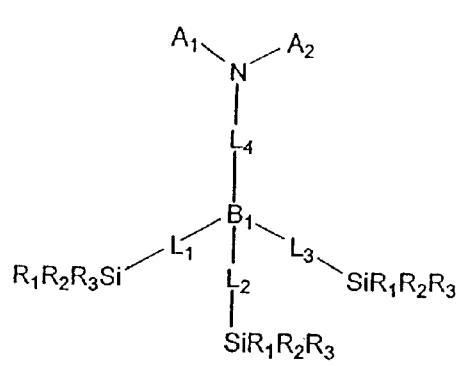
Figure 15:
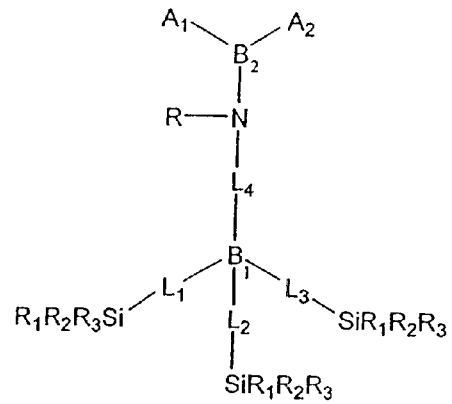
Figure 15:
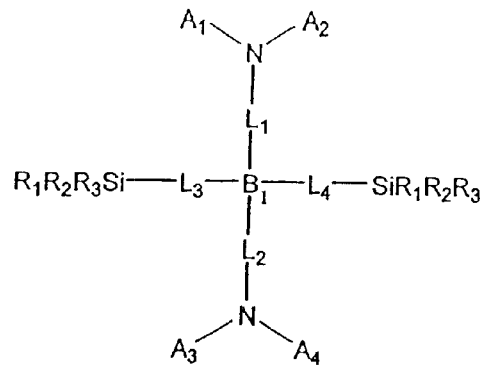

In a further embodiment, compounds of Formulas 17, 18, 19, and 20 shown in FIG. 15 are provided.

In one embodiment of the compounds of Formulas 17–20, $R_1$, $R_2$, $R_3$ are independently a reactive group, such as alkoxy or halide, for example, —$OCH_3$, or —$OCH_2CH_3$, for example, in one embodiment, $R_1$, $R_2$ and $R_3$ are each —$OCH_3$; or in another embodiment, $R_1$ and $R_2$ are independently a reactive group, such as alkoxy or halide, for example —$OCH_3$ or —$OCH_2CH_3$, and $R_3$ is an alkoxy or halide group or an alkyl group, such as —$CH_3$, or substituted alkyl group.

In one embodiment of the compounds of Formulas 17–20, $L_1$, $L_2$, and $L_3$ are independently linear or branched alkyl or heteroalkyl, e.g., C1–25 alkyl, for example, —$(CH_2)_n$—, wherein n=2 to 10, e.g., 3 to 4, or e.g., 2–3. For example, $L_1$, $L_2$, and $L_3$ may optionally comprise a heteroalkyl comprising a heteroatom such as O, S, or N. Each $L_1$, $L_2$, and $L_3$ independently optionally comprise one or more derivatizable groups, e.g., 1–4 derivatizable groups, such as hydroxyl or an amino group.

In one embodiment of Formulas 17–20, $A_1$ and $A_2$ may independently comprise H or a moiety comprising one or more derivatizable functional groups. In one embodiment, $A_1$ and $A_2$ are independently moieties comprising an amino group or a hydroxyl group, such as —$CH_2CH_2OH$. In another embodiment, $A_1$ and $A_2$ may independently comprise, for example, a linear or branched alkyl or heteroalkyl including a plurality of derivatizable functional groups, for example, 1, 2, or 3 derivatizable groups. In one embodiment, $A_1$ and $A_2$ may independently comprise a linear or branched alkyl or heteroalkyl, wherein one or more carbon atoms of the alkyl group is functionalized, for example, to an amide.

In one embodiment of the compounds of Formulas 17–20, $B_1$ and $B_2$ are independently a branching group, for example alkyl, a heteroatom, or heteroalkyl, for example a C1–12 alkyl.

In one embodiment of the compounds of Formulas 17–20, $L_4$ is a direct bond or a linker, for example, C1–12 alkyl or heteroalkyl optionally comprising one more derivatizable groups.

R in one embodiment is H or alkyl or heteroalkyl, for example C1–12 alkyl, or in another embodiment is acyl, for example $HC(=CH_2)CO$— or $MeC(=CH_2)CO$—.

Figure 16:
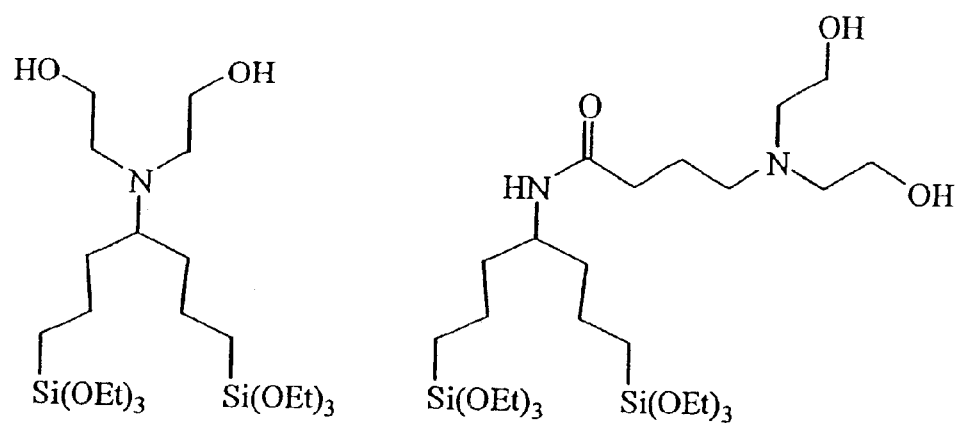
FIG. 16 shows the structure of some exemplary silicon compounds.
Figure 16:
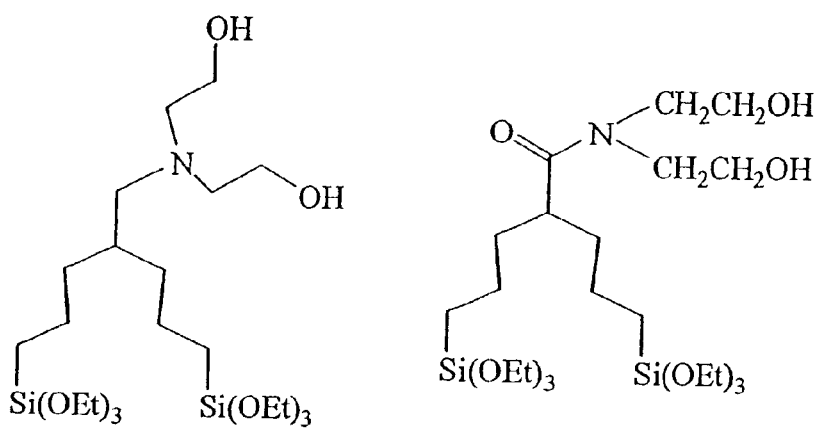
Figure 16:
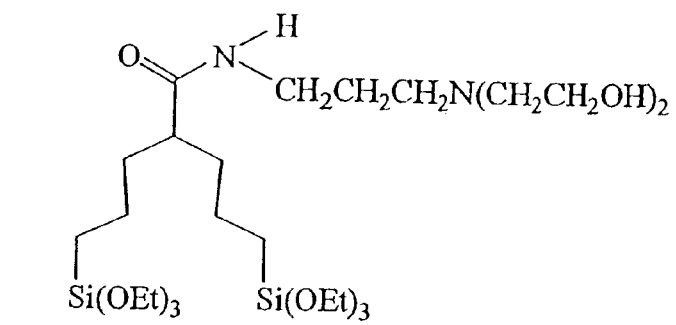
Figure 17:
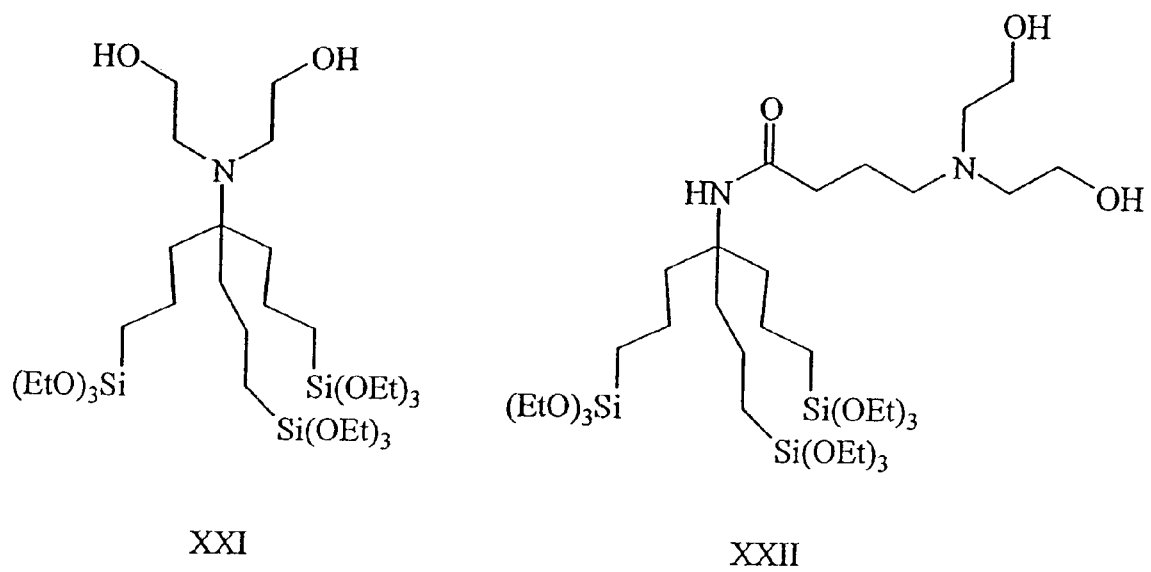
FIG. 17 shows another embodiment of exemplary silicon compounds XXI and XXII.

Examples of compounds of Formula 17 include compounds XIX, XX and XXIV in FIG. 16. Examples of compounds of Formula 19 include compounds XXI and XXII in FIG. 17. Other examples of compounds include compounds XXVII and XXVIII in FIG. 16.

Figure 20:
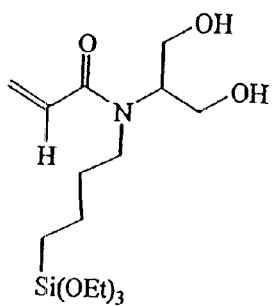
FIG. 20 shows the structure of exemplary silicon compounds XXIa–b, XXIIa–b and XXIIIa–b.
Figure 20:
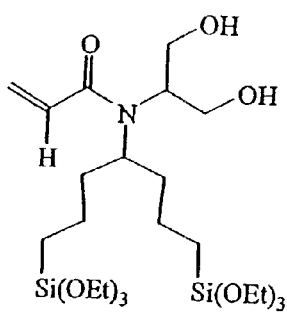
Figure 20:
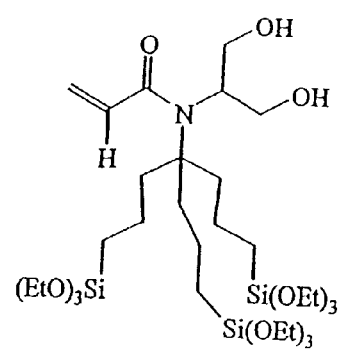
Figure 20:
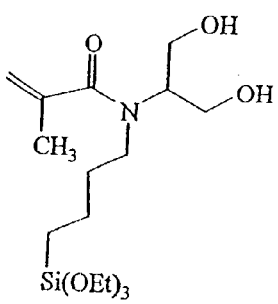
Figure 20:
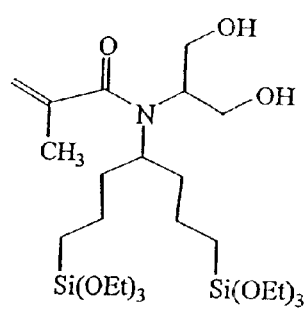
Figure 20:
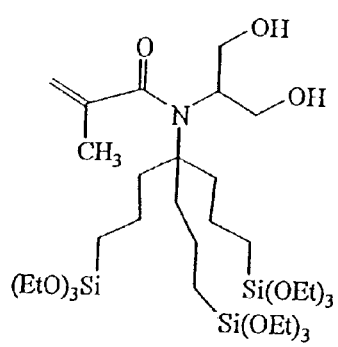

In one embodiment, compounds of Formula 18 include compounds XXXIa and XXXIb shown in FIG. 20. Compounds of Formula 20 include compounds XXXIIa and XXXIIb shown in FIG. 20.

In another embodiment, the compounds may include a single silicon group, as for example compounds XXXIIIa and XXXIIIb shown in FIG. 20.

In another embodiment, compounds of Formula 21 in FIG. 15 are provided, wherein:

In one embodiment of Formula 21, $R_1$, $R_2$, $R_3$ are independently a reactive group, such as alkoxy or halide, for example, —$OCH_3$, or —$OCH_2CH_3$, for example, in one embodiment, $R_1$, $R_2$ and $R_3$ are each —$OCH_3$; or in another embodiment, $R_1$ and $R_2$ are independently a reactive group, such as alkoxy or halide, for example —$OCH_3$ or —$OCH_2CH_3$, and $R_3$ is an alkoxy or halide group or an alkyl group, such as —$CH_3$, or substituted alkyl group.

In one embodiment of Formula 21, $L_1$, $L_2$, $L_3$, and $L_4$ are independently a direct bond, or linear or branched alkyl or heteroalkyl, e.g., C1–25 alkyl, for example, —$(CH_2)_n$—, wherein n=2 to 10, e.g., 3 to 4, or e.g., 2–3. For example, $L_1$, $L_2$, $L_3$ and $L_4$ may optionally comprise a heteroalkyl comprising a heteroatom such as O, S, or N. Each $L_1$, $L_2$, $L_3$ and $L_4$ independently optionally comprise one or more derivatizable groups, e.g., 1–4 derivatizable groups, such as hydroxyl or an amino group.

In one embodiment, $B_1$ is a branching group, for example alkyl, a heteroatom, or heteroalkyl, for example a C1–12 alkyl.

In one embodiment, $A_1$, $A_2$, $A_3$, and $A_4$ may independently comprise H or a moiety comprising one or more derivatizable functional groups. In one embodiment, $A_1$, $A_2$, $A_3$, and $A_4$ are independently a moiety comprising an amino group or a hydroxyl group, such as —$CH_2CH_2OH$. In another embodiment, $A_1$, $A_2$, $A_3$, and $A_4$ may independently comprise, for example, an alkyl, such as a linear or branched alkyl, including a plurality of derivatizable functional groups, for example, 1, 2 or 3 derivatizable groups. In one embodiment, $A_1$, $A_2$, $A_3$, and $A_4$ may independently comprise a linear or branched alkyl or heteroalkyl, wherein one or more carbon atoms of the alkyl group is functionalized, for example, to comprise an amide.

Figure 18:
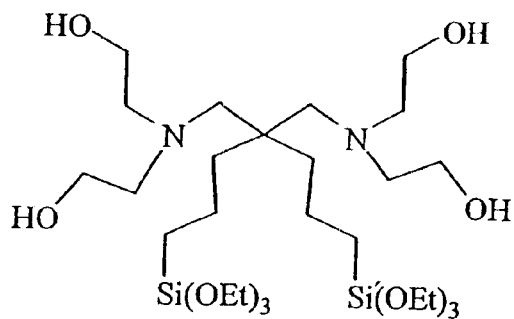
FIG. 18 shows the structure of exemplary silicon compounds XXIII, XXV and XXVI.
Figure 18:
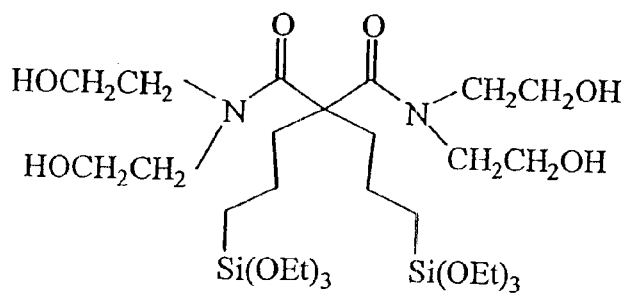
Figure 18:
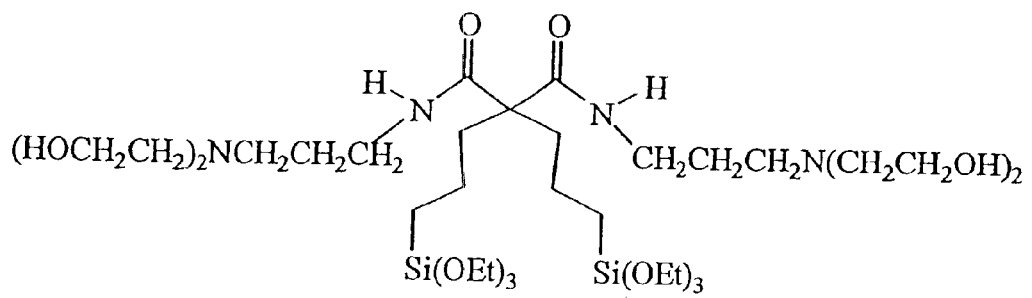

Embodiments of compounds of Formula 21 include compounds XXIII, XXV and XXVI shown in FIG. 18.

In a further embodiment, compounds of Formula 3 are provided:

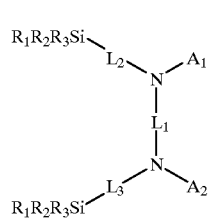

Formula 3

In Formula 3, in one embodiment, $R_1$, $R_2$ and $R_3$ are independently reactive groups, such as alkoxy or halide, for example, —$OCH_3$, or —$OCH_2CH_3$, and wherein, in one embodiment, $R_1$, $R_2$ and $R_3$ are each —$OCH_3$. In one embodiment $R_1$ and $R_2$ are independently a reactive group, such as alkoxy or halide, for example —$OCH_3$ or —$OCH_2CH_3$, and $R_3$ is an alkoxy or halide group or an alkyl group, such as —$CH_3$, or substituted alkyl group.

In Formula 3, in one embodiment, $L_1$, $L_2$, and $L_3$ are independently a linker, for example, a straight chain saturated hydrocarbon, such as —$(CH_2)_n$—, wherein n=1 to 10, or 1 to 5, or, e.g., 2 to 3.

In Formula 3, in one embodiment, $A_1$ and $A_2$ are independently H or moieties comprising one or more derivatizable functional groups, such as hydroxyl or amino groups, or modified forms thereof, such as protected forms. In another embodiment, $A_1$ and $A_2$ each comprise a plurality of derivatizable functional groups. For example, $A_1$ and $A_2$ may each comprise a branched moiety including a plurality of derivatizable functional groups, such as hydroxyl groups.

In one embodiment of Formula 3, $R_1$ and $R_2$ are independently alkoxy or halide; $R_3$ is alkoxy, halide or alkyl; $L_1$, $L_2$, and $L_3$ are independently —$(CH_2)_n$—, wherein n is 2–10; and $A_1$ and $A_2$ are independently a moiety comprising one or more derivatizable functional groups.

In another embodiment of Formula 3, $A_1$ is —$L_4$—$G_1$ and $A_2$ is —$L_5$-$G_2$; $R_1$ and $R_2$ are independently alkoxy or halide; $R_3$ is alkoxy, halide or alkyl; $L_1$, $L_2$, $L_3$, $L_4$ and $L_5$ are —$(CH_2)_n$—, wherein n is 1 to 10, for example 2 to 3; and $G_1$ and $G_2$ are independently a moiety comprising one or more derivatizable functional groups. In another embodiment, $L_1$, $L_4$, and $L_5$ are —$(CH_2)_2$—, $L_2$ and $L_3$ are —$(CH_2)_3$—, and $G_1$ and $G_2$ are —OH.

In another embodiment, silicon compounds of Formula 15 in FIG. 10 are provided, wherein $R_1$, $R_2$ are independently alkoxy, for example —$OCH_3$ or —$OCH_2CH_3$, or halide; and $R_3$ is alkoxy, alkyl, or halide.

In a further embodiment, compounds of Formula 6a in FIG. 1 are provided, wherein n is 1–3, for example 2 or 3.

Exemplary functionalized silicon compounds include compound V below, and compound VI shown in FIG. 1.

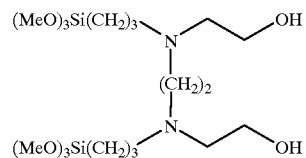

V

Another embodiment is illustrated in FIG. 7, which shows a compound of Formula 10, wherein n=1 to 10, e.g., 1–3, and G is a derivatizable functional group, such as hydroxyl, protected hydroxyl, or halide such as Cl or Br.

Figure 2:
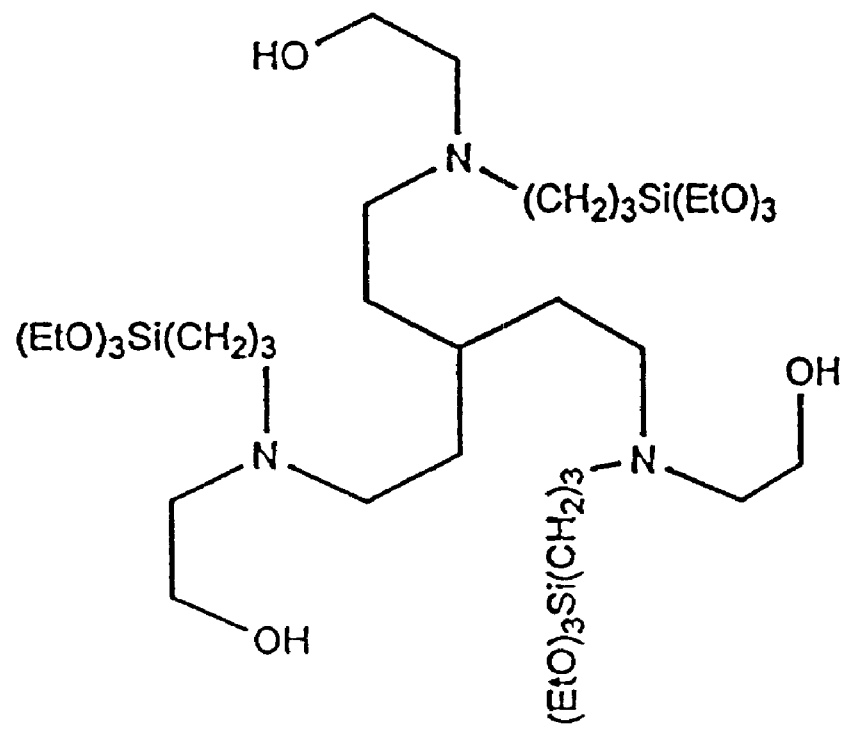
FIG. 2 shows the structure of the functionalized silicon compound VIII.

The hydrolytic stability of the silicon compound coating may be increased by increasing the number of covalent bonds to the surface of the support. For example, silicon compounds II–V include two activated silicon groups for binding to a support surface, such as glass. A variety of functionalized silicon compounds including a plurality of activated silicon groups and derivatizable functional groups are useful to form functionalized coatings. A further example is compound VII shown in FIG. 1. Another example is silicon compound VIII shown in FIG. 2, which can form up to three covalent bonds to the surface of a glass support. In compound VIII, the triethoxysilyl group is shown by way of example, however alternatively, the activated silicon group may be other activated silicon groups or mixtures thereof, such as trimethoxysilyl. Similarly, in all of the silicon compounds disclosed herein in which a representative activated silicon group, such as trimethoxysilyl, is substituted on the compound, the compounds in other embodiments also may be substituted with other activated silicon groups known in the art and disclosed herein.

The silicon compounds II–VIII having multiple silicon groups enhance potentially by twice as much, or more, the hydrolytic stability in comparison to silicon compounds comprising only a single silicon group, since they possess more trialkoxysilyl groups that can react, and form bonds with, a surface. The number of silicon groups in the silicon compound may be modified for different applications, to increase or decrease the number of bonds to a support such as a glass support. Silcon compounds may be used that form optimally stable surface-bonded films on glass via covalent siloxane bonds. Additionally, the number of derivatizable functional groups may be increased or decreased for different applications, as illustrated by silicon compounds II–VIII. Silicon compounds may be selected for use that provide the desired optimum density of surface derivatizable groups, such as hydroxyalkyl groups, for a desired application, such as the synthesis of nucleic acid arrays, or for the optimum stability during use of the array in different applications.

Figure 5:
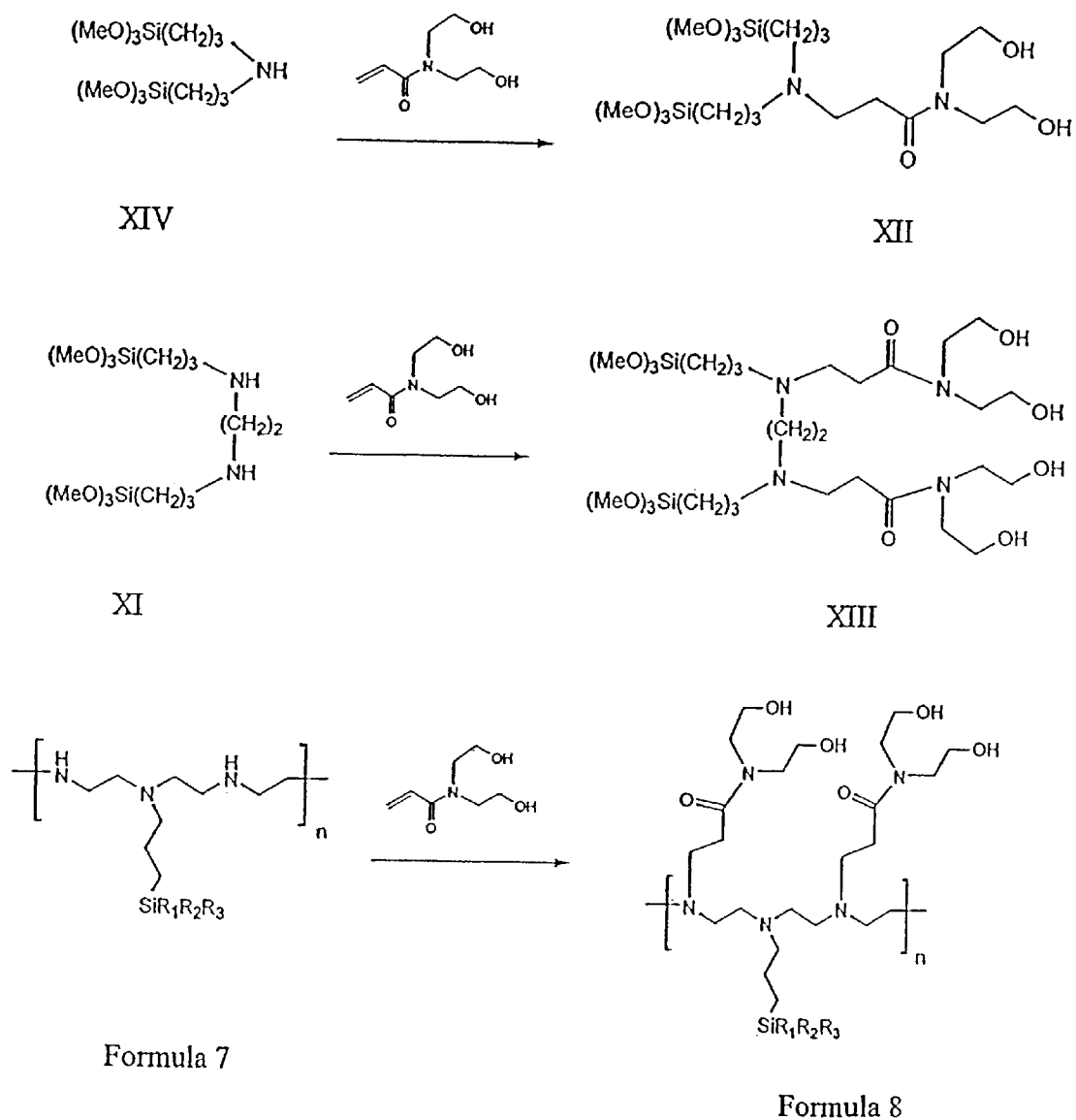
FIG. 5 show schemes for the synthesis of compounds XII, XIII and compounds of Formula 8.

Other embodiments of functionalized silicon compounds include compound XIII shown in FIG. 5.

In another embodiment, polymeric functionalized silicon compounds of Formula 4 are provided:

Formula 4

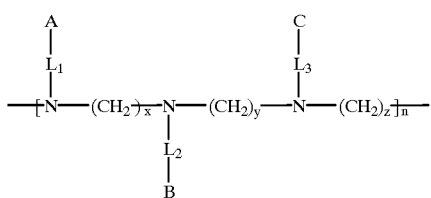

In Formula 4, in one embodiment, x, y and z are independently 1–3 and, in one embodiment, x, y and z are each 2.

In Formula 4, in one embodiment, $L_1$, $L_2$ and $L_3$ are independently linkers, for example, straight chain hydrocarbons, and preferably —$(CH_2)_m$—, wherein m=1–10, e.g., 2–3.

In Formula 4, in one embodiment, at least one of A, B and C is —$SiR_1R_2R_3$, wherein $R_1$ and $R_2$ are independently a reactive group, such as alkoxy or halide, for example, —$OCH_3$, or —$OCH_2CH_3$ and $R_3$ is alkoxy, halide or alkyl; and wherein the remainder of A, B and C are independently moieties comprising one or more derivatizable functional groups, such as hydroxyl groups, or amino groups, or modified forms thereof, such as protected forms, for example —OH or a branched molecule comprising one or more hydroxyl groups.

In Formula 4, in one embodiment, n is, for example, about 10 to 10,000, or, for example, about 1,000 to 10,000.

In one embodiment of Formula 4, B is —$SiR_1R_2R_3$, wherein $R_1$, $R_2$ and $R_3$ are independently alkoxy, halide or alkyl; x, y, and z are independently 2–3; $L_1$, $L_2$ and $L_3$ are independently —$(CH_2)_m$—, wherein m is 2–3; A and C are independently moieties comprising derivatizable functional groups; and n is about 10 to 10,000.

In one embodiment of Formula 4, B is —$Si(OCH_3)_3$; x, y, and z are 2; $L_1$ and $L_3$ are —$(CH_2)_2$—; $L_2$ is —$(CH_2)_3$—; A and C are moieties comprising derivatizable functional groups; and n is about 10 to 10,000.

Figure 4:
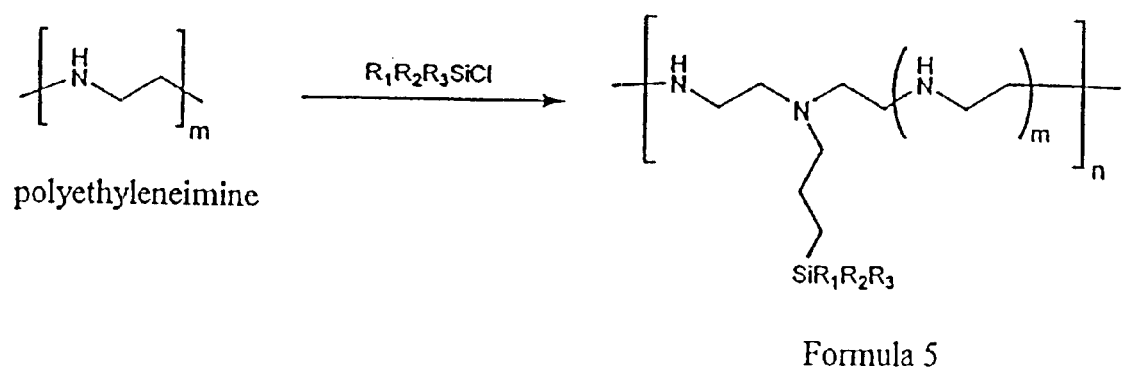
FIG. 4 is a scheme showing the synthesis of compounds of Formula 5 or 6.
Figure 4:
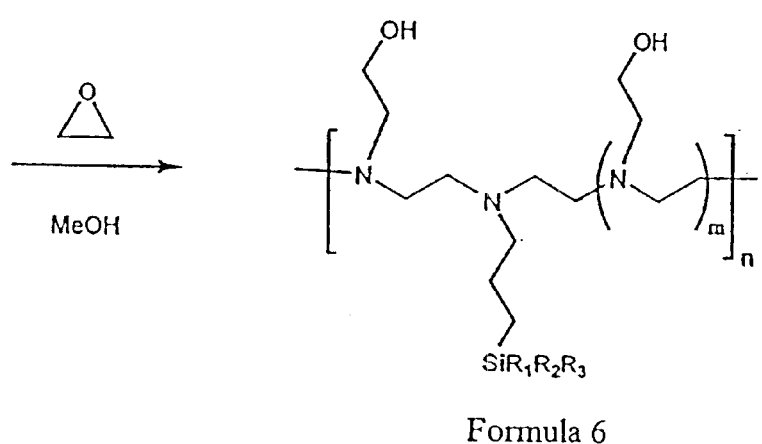

Other embodiments of a polymeric functionalized silicon compound include compounds of Formula 5 and 6 shown in FIG. 4, wherein m is about 0 to 10, e.g., about 1 to 5, and n is about 10 to 10,000. In Formulas 5 and 6, $R_1$ and $R_2$ are independently a reactive group, such as alkoxy or halide, for example, —$OCH_3$ or —$OCH_2CH_3$, and $R_3$ is a reactive group, such as alkoxy or halide, or optionally alkyl, for example —$CH_3$.

Figure 6:
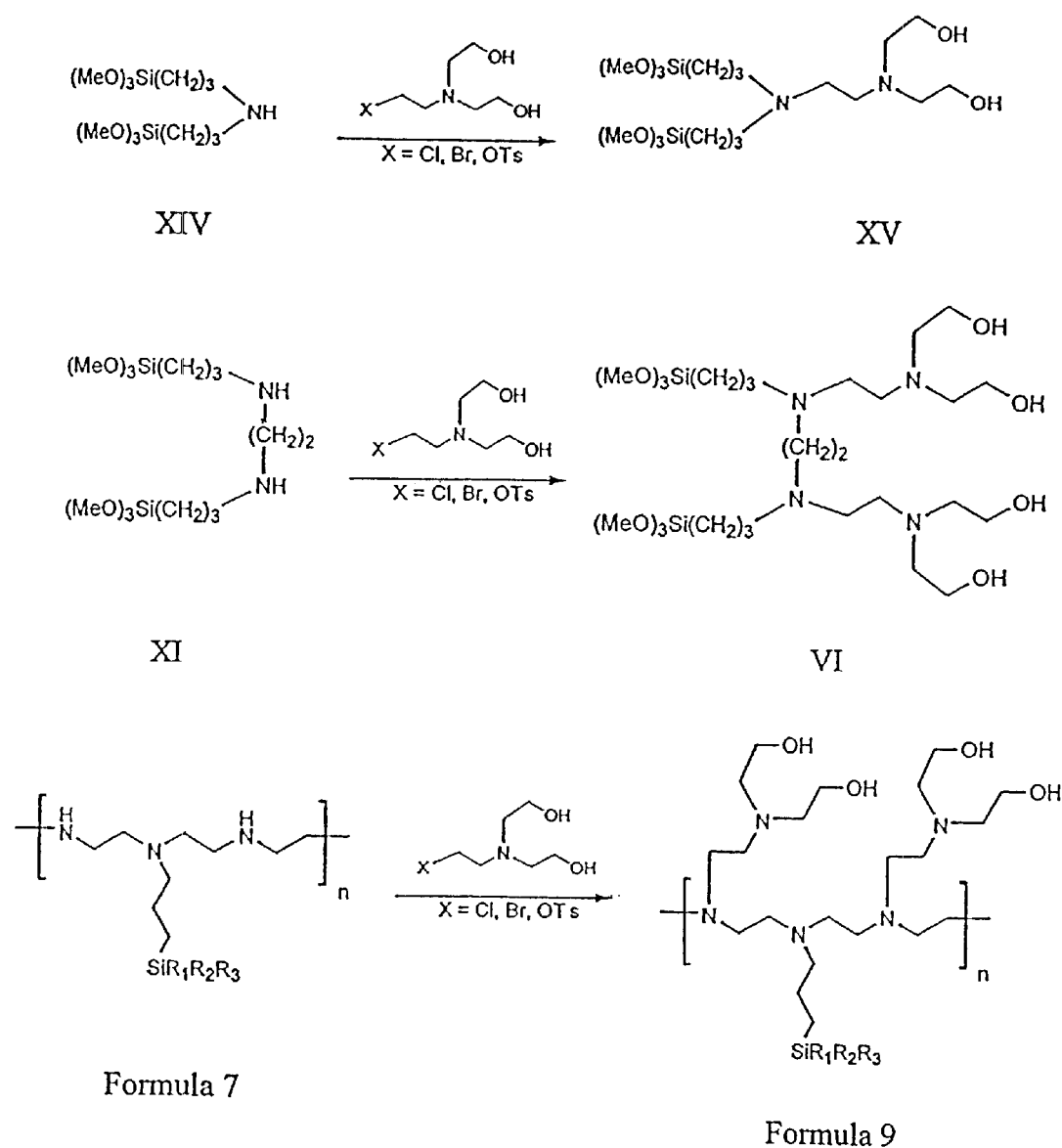
FIG. 6 shows schemes for the synthesis of compounds XV, VI and compounds of Formula 9.

Other embodiments include compounds of Formula 7 and 8, shown in FIG. 5, and Formula 9, shown in FIG. 6, wherein n is about 10 to 10,000. In Formulas 7, 8 and 9, $R_1$ and $R_2$ are independently a reactive group, such as alkoxy or halide, for example, —$OCH_3$ or —$OCH_2CH_3$, and $R_3$ is a reactive group such as alkoxy or halide or optionally alkyl, for example —$CH_3$.

Figure 8:
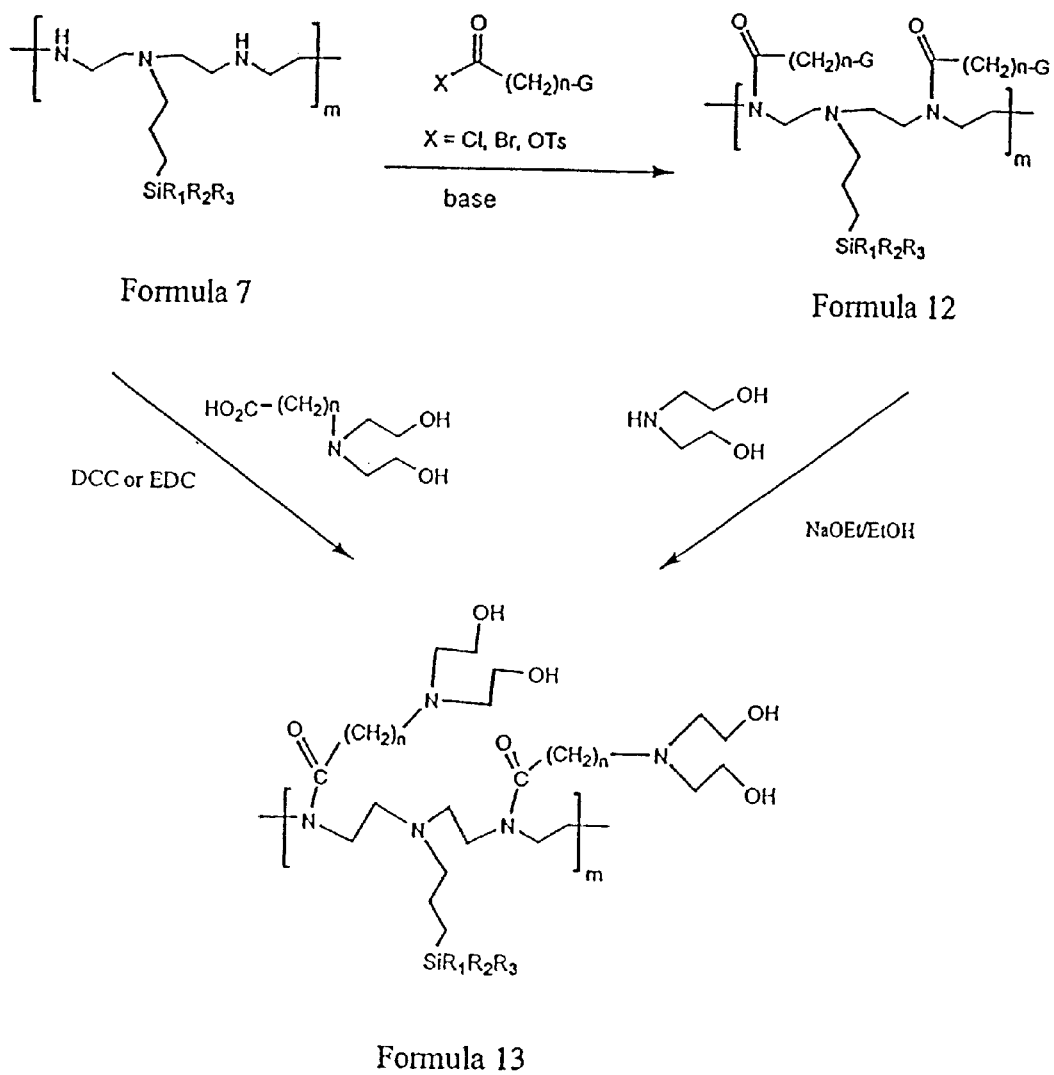
FIG. 8 shows schemes showing the synthesis of compounds of Formula 12 or 13.

Further embodiments include compounds of Formula 12 and 13, shown in FIG. 8, wherein m is about 10 to 10,000, and n is about 1 to 10, e.g., about 5 to 10. In Formulas 12 and 13, $R_1$ and $R_2$ are independently a reactive group, such as alkoxy or halide, for example, —$OCH_3$ or —$OCH_2CH_3$, and $R_3$ is a reactive group, such as alkoxy or halide, or optionally alkyl, for example —$CH_3$. In Formula 12, G is a substitutable leaving group, such as hydroxy, protected hydroxy, or halo, such as —Cl or —Br.

The use of a polymer permits the formation of stable films on surfaces, such as glass, due to the very large number of siloxane bonds that can be formed with the surface. The number of alkoxysilicon groups relative to the number of hydroxyalkyl groups can be selected to provide the desired density of reactive hydroxyl groups.

Synthesis of Functionalized Silicon Compounds

Functionalized silicon compounds for use in the methods described herein are available commercially, or may be synthesized from commercially available starting materials. Commercially available silicon compounds and a review of silicon compounds is provided in Arkles, Ed., "Silicon, Germanium, Tin and Lead Compounds, Metal Alkoxides, Diketonates and Carboxylates, A Survey of Properties and Chemistry," Gelest, Inc., Tullytown, Pa., 1995, the disclosure of which is incorporated herein. Functionalized silicon compounds may be synthesized using methods available in the art of organic chemistry, for example, as described in March, *Advanced Organic Chemistry*, John Wiley & Sons, New York, 1985, and in R. C. Larock, *Comprehensive Organic Transformations*, Wiley-VCH, New York, 1989.

Methods of synthesizing compounds of Formula 1 are shown in Scheme I below. Commercially available reagents which may be used in syntheses in accordance with Scheme I include 3-chloro-1-triethoxysilylpropane and ethylene oxide (Aldrich®, Milwaukee, Wis.).

Scheme I

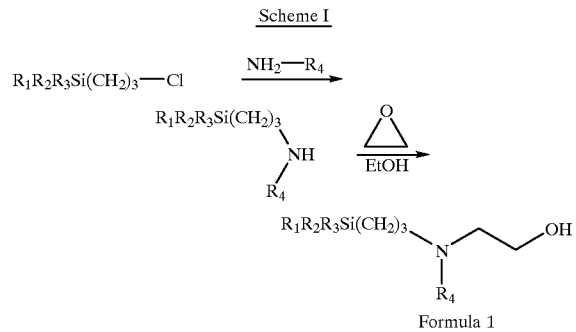

A method for the conversion of bis (trimethoxysilylpropyl)amine, XIV, which is commercially available from Gelest, Inc. (Tullytown, Pa.) to compound II is illustrated below in Scheme II.

Scheme II

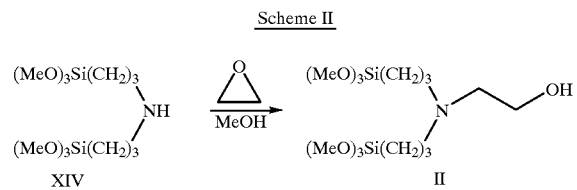

A method for the conversion of compound XI, bis[3-trimethoxysilyl)propyl]-ethylenediamine, which is commercially available from Gelest, Inc., Tullytown, Pa., to compound V is shown below in Scheme III.

Scheme III

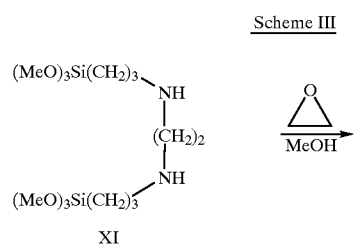

-continued

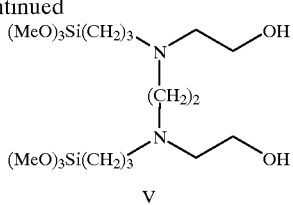

V

A method for the synthesis of compound III is shown below in Scheme IV. The reagents shown in Scheme IV are commercially available from Aldrich® (Milwaukee, Wis.).

Scheme IV

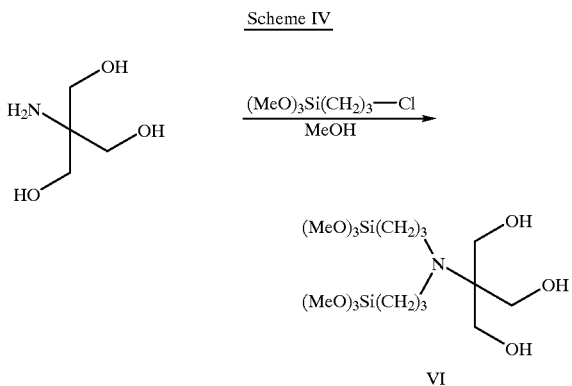

VI

Figure 3:
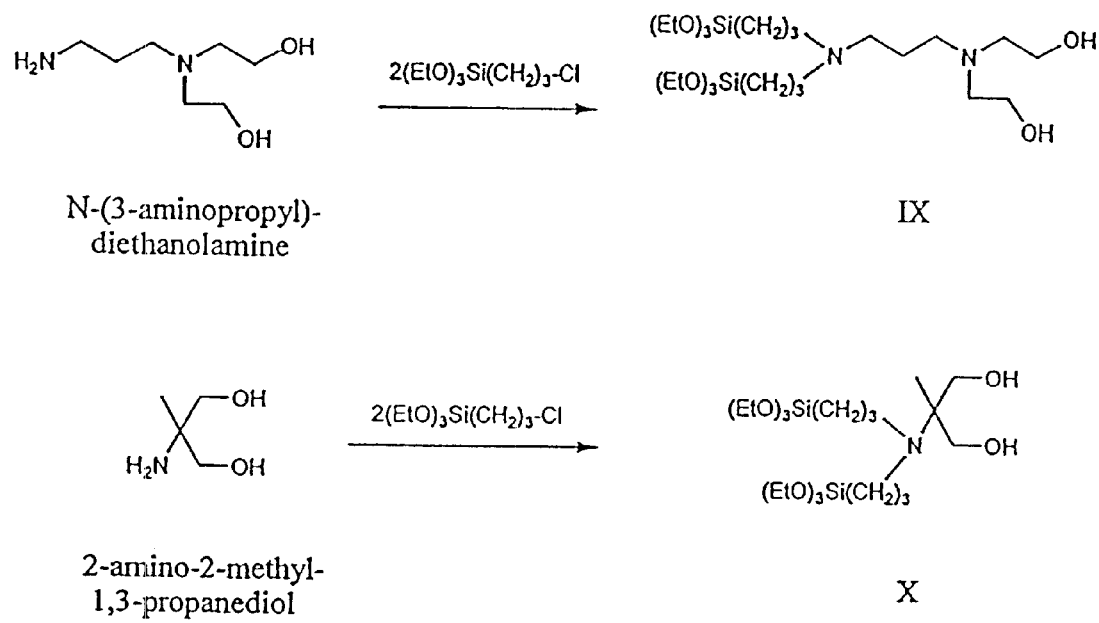
FIG. 3 shows schemes for the synthesis of compounds IX and X.
Figure 9:
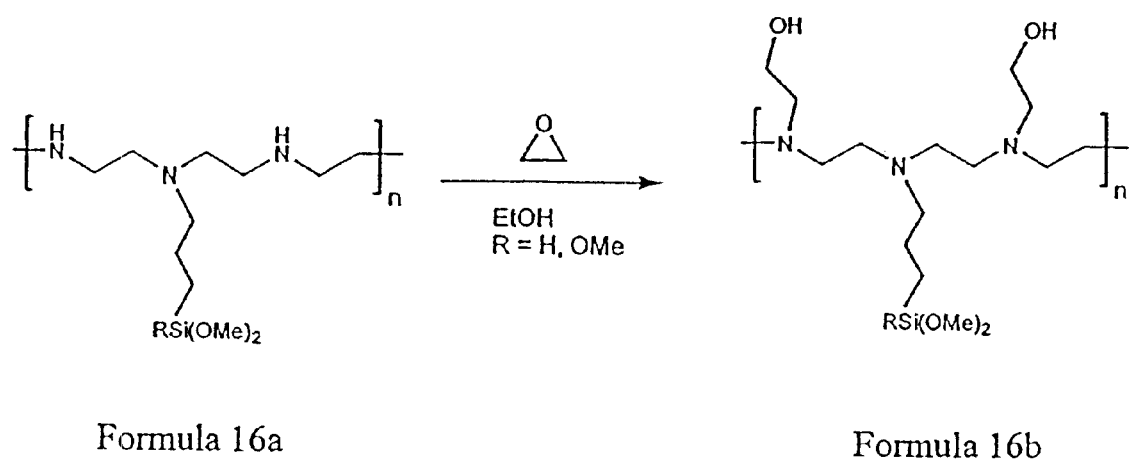
FIG. 9 is a scheme of the synthesis of compounds of Formula 16b.

Reaction schemes for the synthesis of functionalized silicon compounds IX and X are provided in FIG. 3. Reaction schemes for the synthesis of compounds of Formulas 5 and 6 are shown in FIG. 4. Polyethyleneimine is available commercially, for example, from Aldrich®. Polyamines of Formula 5, where $R_1$, $R_2$ and $R_3$ are OMe (trimethoxysilylpropyl modified (polyethyleneimine)), or $R_1$ is Me and $R_2$ and $R_3$ are OMe (dimethoxymethylsilylpropyl modified (polyethylenimine)) are available from Gelest (Tullytown, Pa.). FIG. 9 shows another embodiment of a reaction scheme using commercially available reagents, wherein the compound of Formula 16a is converted to the compound of Formula 16b.

Reaction schemes for the synthesis of compounds XII, XIII, and compounds of Formula 8 are shown in FIG. 5. Synthesis of the reagent, N,N-bis(2-hydroxyethyl) acrylamide is described in U.S. Pat. No. 3,285,886 (1966), the disclosure of which is incorporated herein.

Reaction schemes for the synthesis of functionalized silicon compounds XV, VI and compounds of Formula 9 are shown in FIG. 6. Use of the reagent N,N-bis(2-hydroxyethyl)-2-chloro-ethylamine is described in Okubo et al., Deutsches Patent 2144759 (1971), the disclosure of which is incorporated herein.

FIG. 7 illustrates reaction schemes for the synthesis of compounds of Formulas 10 and 11. The use of the reagent, 4-chlorobutanoyl chloride, is described in Njoroge et al., PCT US97/15899 (1998), the disclosure of which is incorporated herein. Other reagents include lactones, such as γ-butyrolactone, δ-valerolactone, and ε-caprolactone (Aldrich®). Compounds XI and XIV are commercially available from Gelest.

FIG. 8 illustrates reaction schemes for compounds of Formulas 12 and 13. In FIG. 8, G is a substitutable leaving group such as halo. Reagents in addition to those discussed above that may be used in syntheses which may be conducted as shown in FIG. 8 include diethanolamine and N,N-bis(2-hydroxyethyl)glycine, which are commercially available, for example, from Aldrich®.

Further exemplary reaction schemes are shown in FIGS. 13 and 14. FIGS. 13 and 14 illustrate examples of methods of synthesis of compounds of Formula 2, compounds XVIa–e, and XVIIa–f. FIG. 13 illustrates examples of methods of synthesis where a compound containing a primary amino function reacts with two equivalents of (3-glycidoxypropyl)trimethoxysilane (available from Gelest, Inc., Tullytown, Pa.) to provide tertiary amine containing compounds XVIa–XVIe. FIG. 14 illustrates examples of methods of synthesis where a compound containing a primary amino function reacts with a carbamoyl chloride (produced by reaction of XIV with triphosgene or other phosgene synthon) to produce the substituted urea compounds XVIIa–XVIIf.

Figure 21:
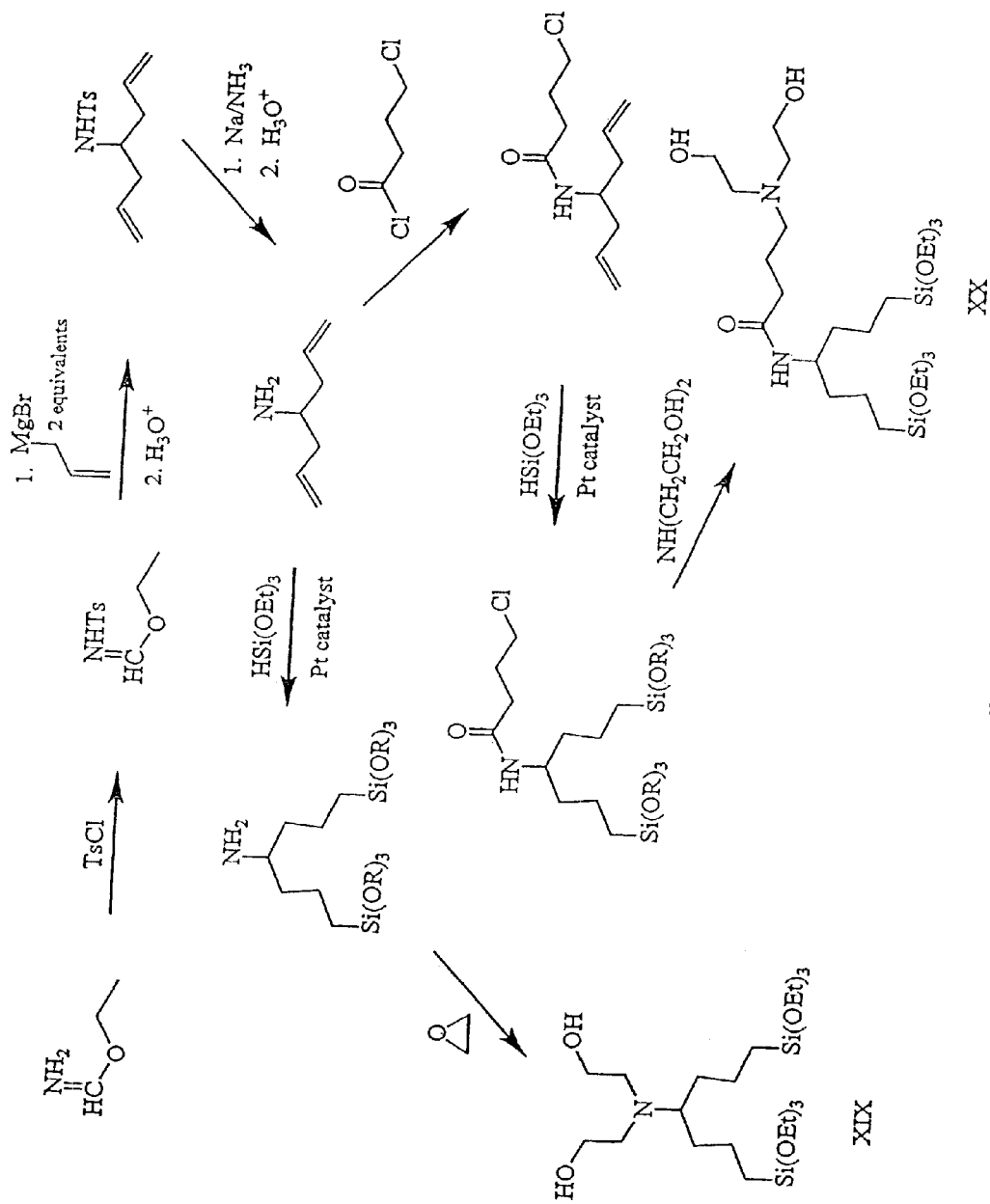
FIG. 21 is a scheme showing the synthesis of silicon compounds XIX and XX.

FIG. 21 provides an exemplary reaction scheme for compounds of Formula 17. The exemplary compounds XIX and XX are synthesized through the common intermediate 4-amino-1,6-heptadiene. This intermediate is prepared from ethylformimidate and methylmagnesium bromide (both available from Aldrich, Milwaukee, Wis.); the preparation is described in Barbot, F.; *Tetrahedron Lett.* 1989, 30, 185 and Barber, H. J.; *J. Chem. Soc.* 1943, 10. Hydrosilylation of 4-amino-1,6-heptadiene followed by reaction with ethylene oxide provides XIX. Acylation of 4-amino-1,6-heptadiene with 4-chlorobutyryl chloride (Aldrich, Milwaukee, Wis.) followed by hydrosilylation, and subsequent reaction of the resulting disilane with diethanol amine affords XX.

Figure 22:
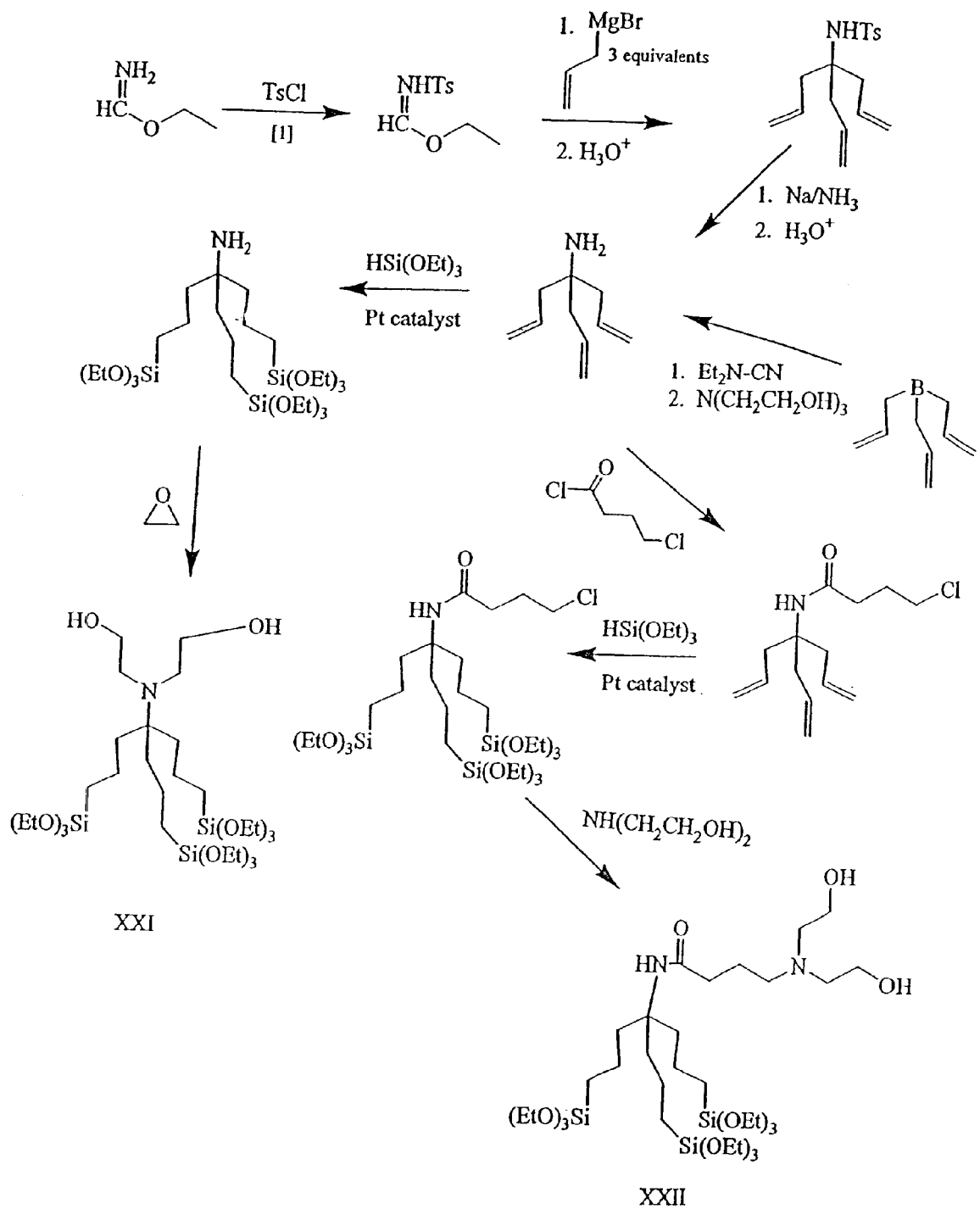
FIG. 22 is a scheme showing the synthesis of silicon compounds XXI and XXII.

FIG. 22 provides an exemplary reaction scheme for compounds of Formula 19. The exemplary compounds XXI and XXII are synthesized through the common intermediate 4-allyl-4-amino-1,6-heptadiene. This intermediate can be prepared, for example, from ethylformimidate and methylmagnesium bromide (both available from Aldrich, Milwaukee, Wis.); the preparation is described in Barbot, F., *Tetrahedron Lett.* 1989, 30, 185; and Barber, H. J., *J. Chem. Soc.* 1943, 101. The intermediate also may be prepared from triallylborane as described in Bubnov, Y. N., et al., *Russian Chem. Bull.* 1996, 45, 2598. Hydrosilylation of 4-ally-4-amino-1,6-heptadiene followed by reaction with ethylene oxide provides XXI. Acylation of 4- allyl-4-amino-1,6-heptadiene with 4-chlorobutyryl chloride (Aldrich, Milwaukee, Wis.) followed by hydrosilylation, and subsequent reaction of the resulting trisilane with diethanol amine affords XXII.

Figure 23:
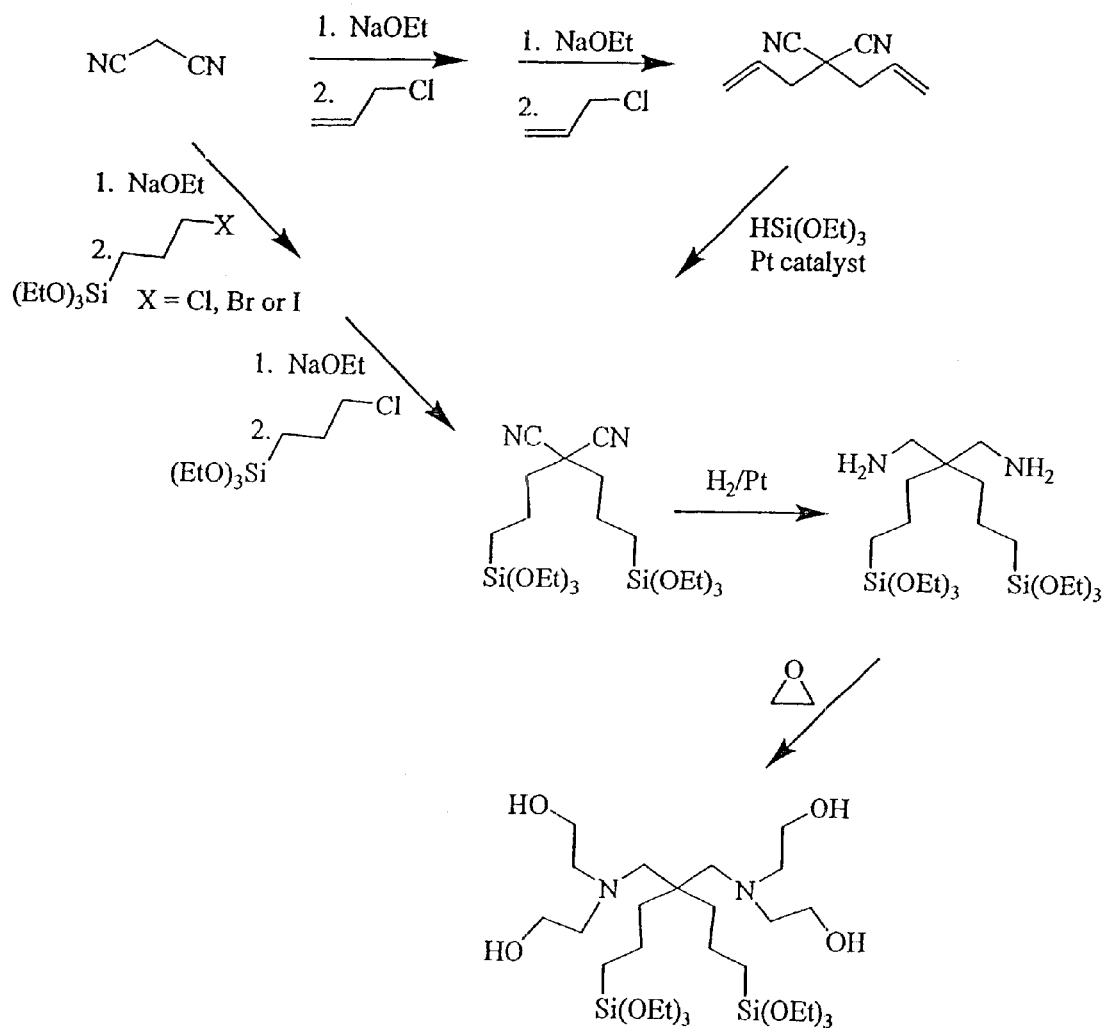
FIG. 23 is a scheme showing the synthesis of silicon compound XXIII.

FIG. 23 provides an exemplary reaction scheme for compounds of Formula 21, including structure XXIII. This compound is prepared by catalytic hydrogen reduction of 4,4-dicyano-1,6-bis(triethoxysilyl)heptane followed by reaction of the resultant diamine with ethylene oxide. The dicyano intermediate is prepared, for example, by a malonitrile synthesis of 4,4-dicyano-1,6-heptadiene followed by hydrosilylation, or by alkylation of malonitrile with 2 equivalents of a 3-halo-1-(triethoxysilyl)propane compound.

Figure 24:
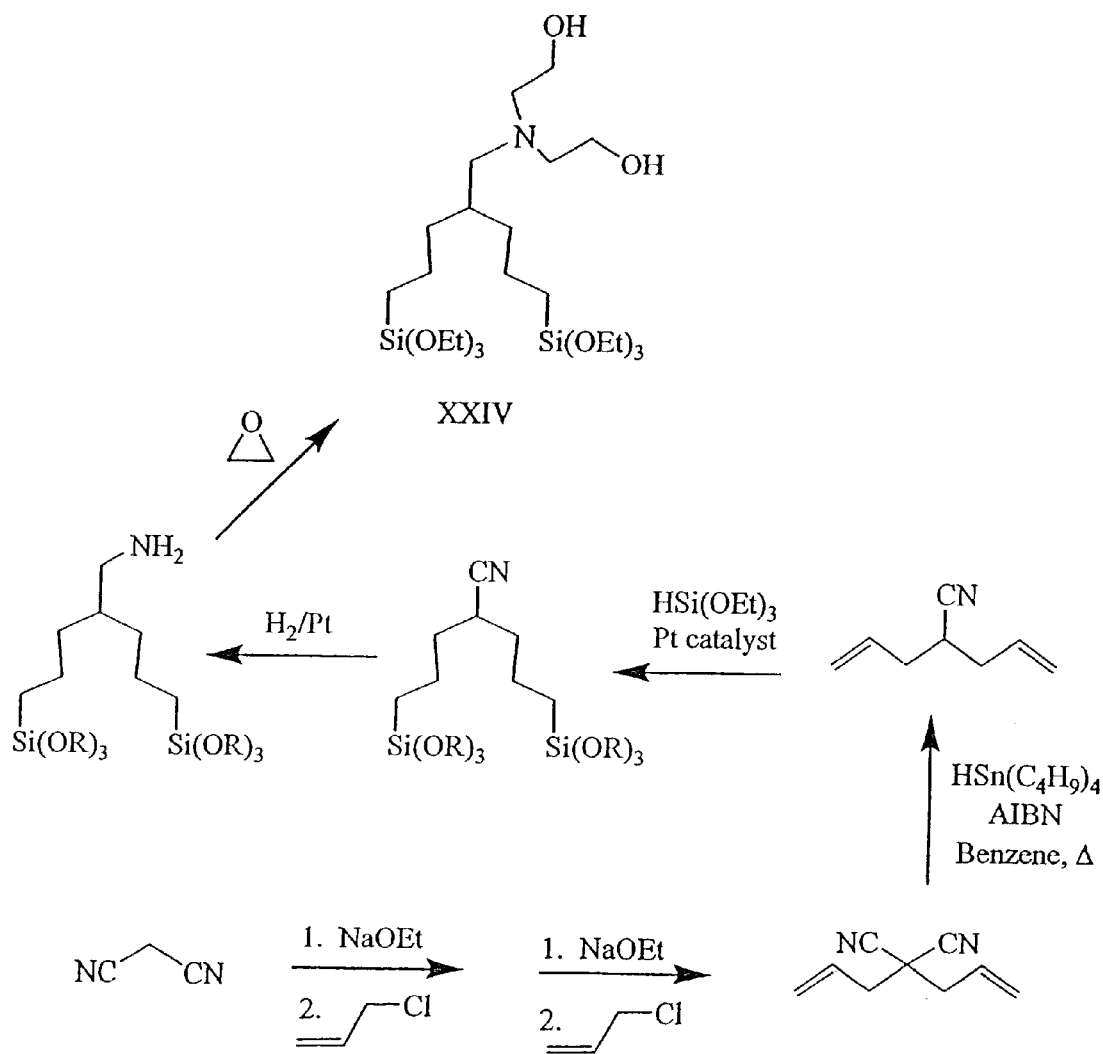
FIG. 24 is a scheme showing the synthesis of silicon compound XXIV.

FIG. 24 provides an exemplary reaction scheme for a compound of Formula 17, including structure XXIV. This compound is prepared by catalytic hydrogen reduction of 4-cyano-1,6-bis(triethoxysilyl)heptane followed by reaction of the resultant amine with ethylene oxide. The cyano intermediate is prepared starting from a malonitrile synthesis of 4,4-dicyano-1,6-heptadiene followed by conversion to 4-cyano-1,6-heptadiene by reduction with an organotin reagent as described in Curran, D. P.; et al., *Synthesis,* 1991, 107. Hydrosilylation of this diene provides 4-cyano-1,6-bis (triethoxysilyl)heptane.

Figure 25:
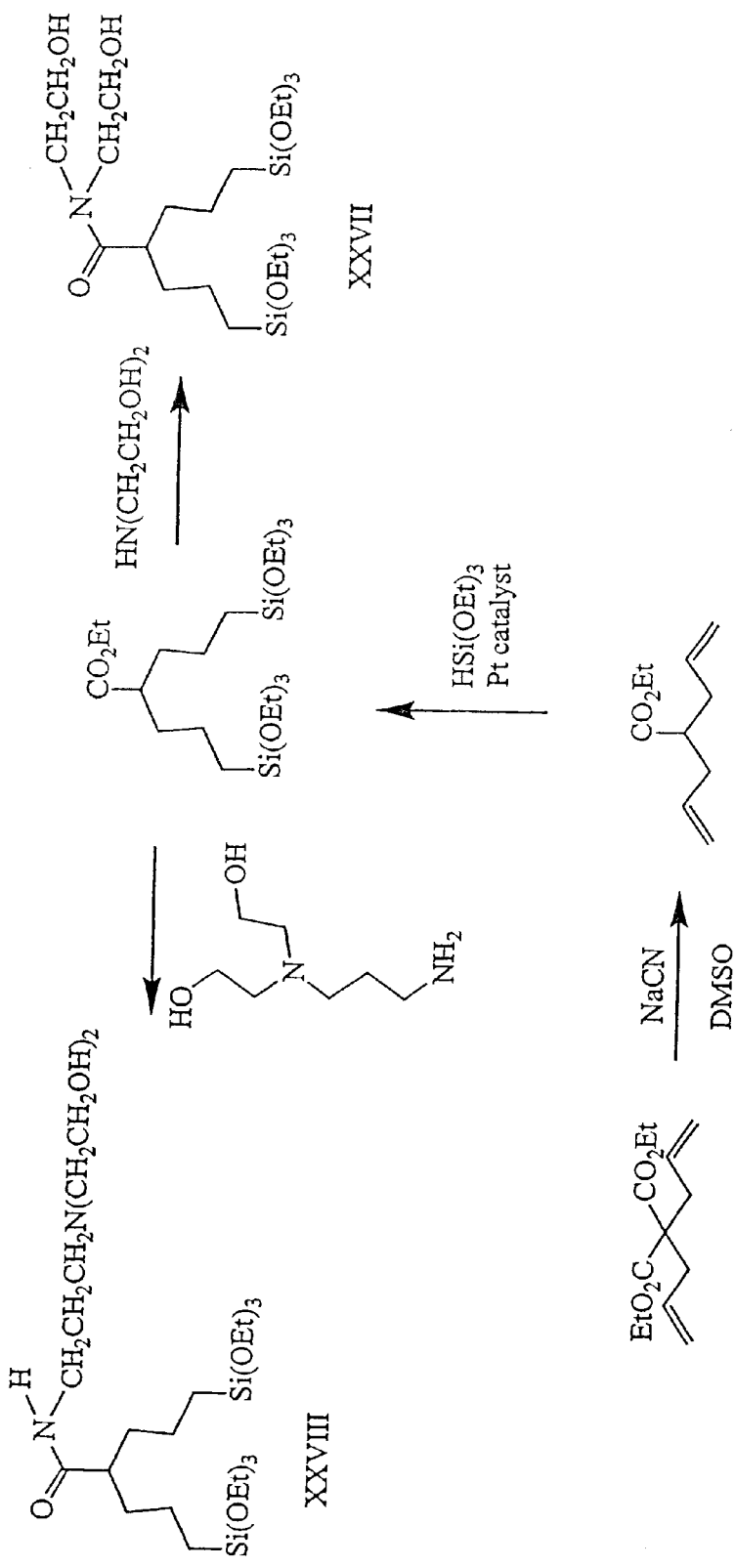
FIG. 25 is a scheme showing the synthesis of silicon compound XXVIII.

FIG. 25 provides an exemplary reaction scheme for compounds of Formula 19, for example, structures XXVII and XXVIII. These compounds are prepared by reaction of appropriate primary (XXVIII) or secondary (XXVII) amines with ethyl 1,7-bis(triethoxysilyl)-4-heptanoate. The ester precursor is synthesized starting from diethyl 2,2-diallylmalonate (Aldrich, Milwaukee, Wis.); the diester is decarboxylated following the method of Beckwith, A. C. J.; et al., *J. Chem. Soc., Perkin Trans. II,* 1975, 1726, to produce ethyl 4-hepta-1,6-dieneoate; the triethoxysilyl moieties are introduced by hydrosilylation.

Figure 26:
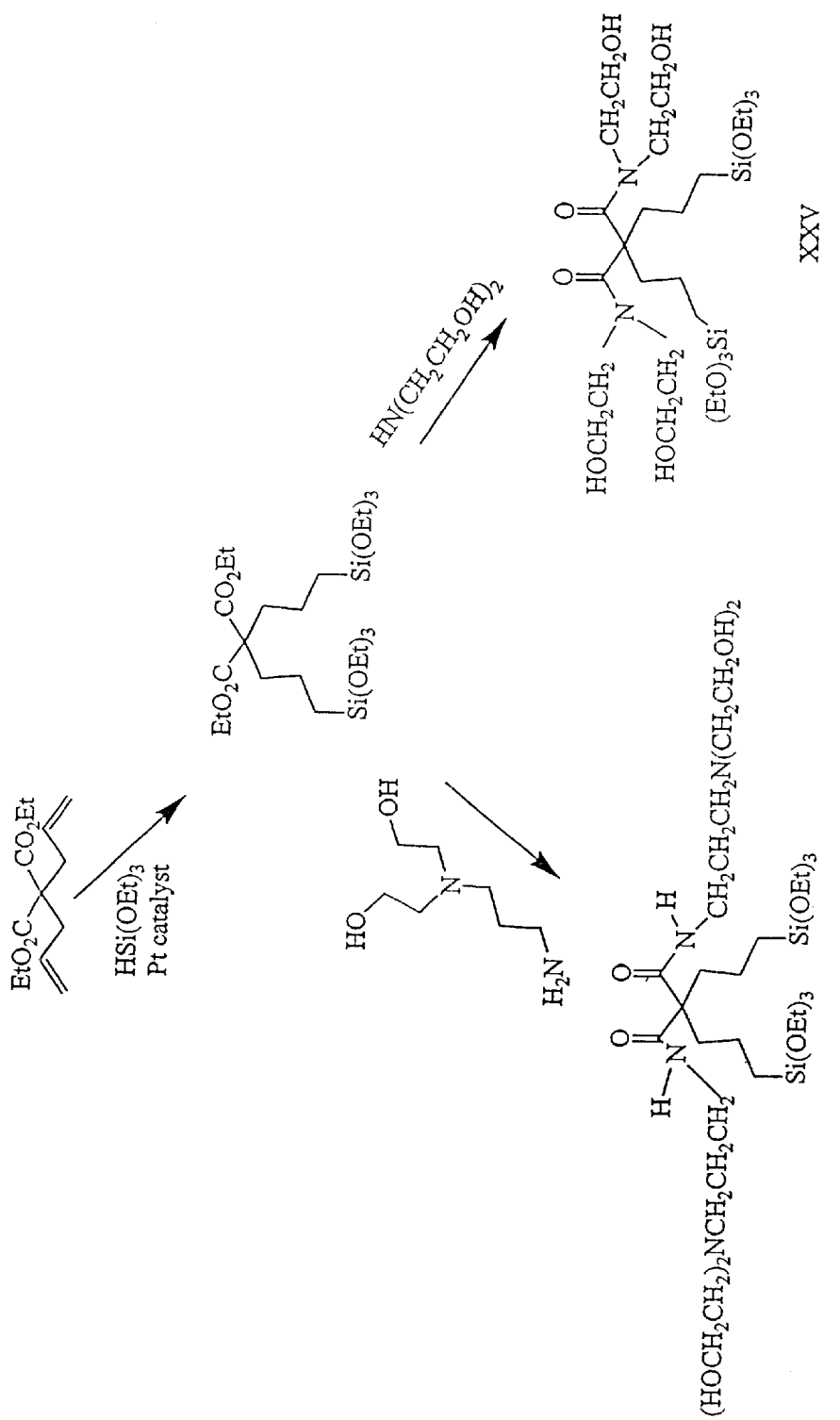
FIG. 26 is a scheme showing the synthesis of silicon compounds XXVI and XXV.

FIG. 26 provides an exemplary reaction scheme for compounds of Formula 21, for example, structures XXV and XXVI. These compounds are prepared by reaction of appropriate primary (XXVI) or secondary (XXV) amines with diethyl 2,2-bis(3-triethoxysilylpropyl)malonate. The diester precursor can be synthesized by hydrosilylation of diethyl 2,2-diallylmalonate (Aldrich, Milwaukee, Wis.).

Figure 27:
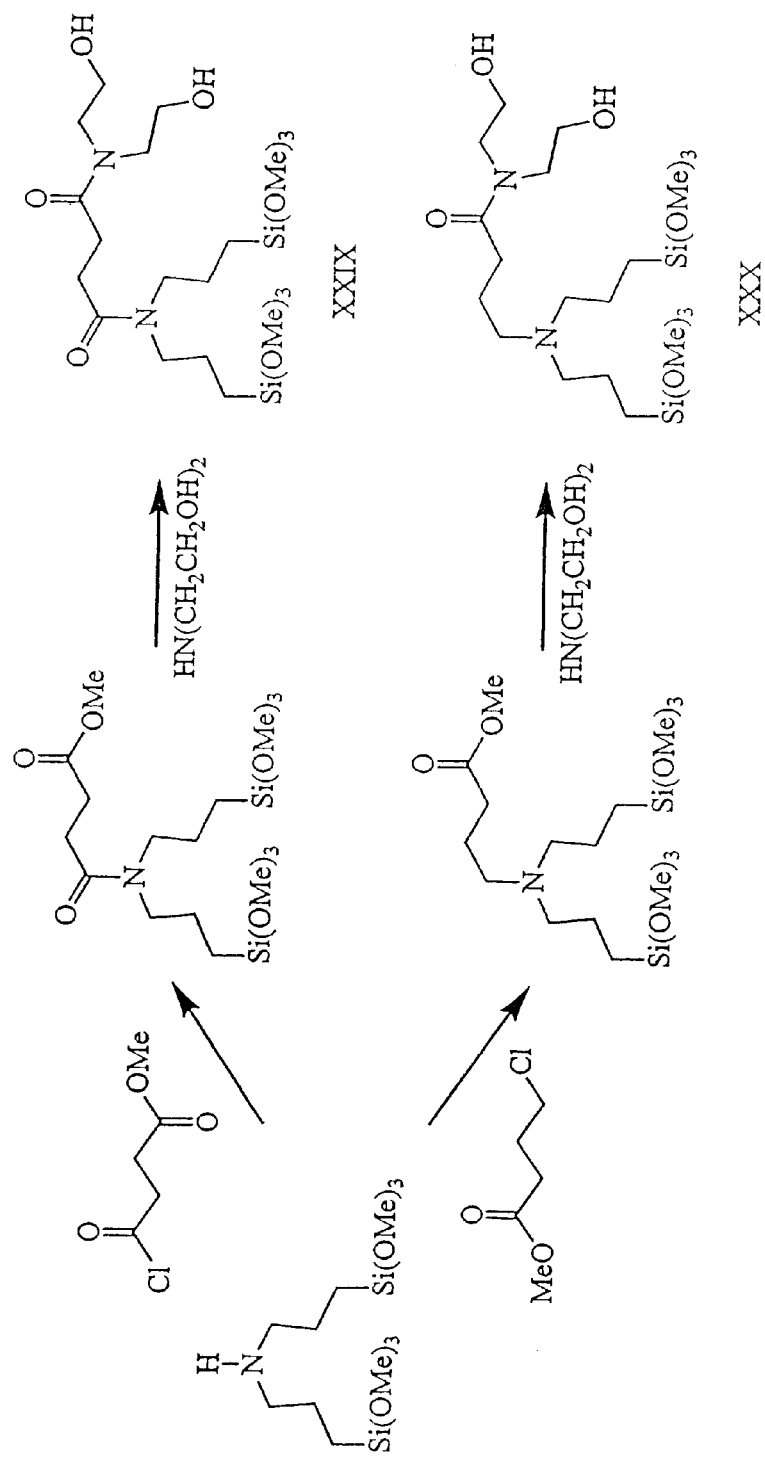
FIG. 27 is a scheme showing the synthesis of silicon compounds XXIX and XXX.

Another embodiment of a synthesis of a compound of Formula 2 is shown in FIG. 27, wherein the synthesis of compounds XXIX and XXX is shown. The general method illustrated here is to N-alkylate (XXX) or N-acylate (XXIX) bis(3-trimethoxypropyl)amine (compound XI, Gelest, Inc., Tullytown, Pa.) with a alkyl chain containing an ester of a carboxylic acid that can be subjected to aminolysis with dihydroxyethylamine (Aldrich, Milwaukee, Wis.). The alkylating agent, methyl 4-chlorobutyrate, and the acylating agent, methyl 4-chloro-4-oxobutyrate, are available from Aldrich (Milwaukee, Wis.).

Figure 28:
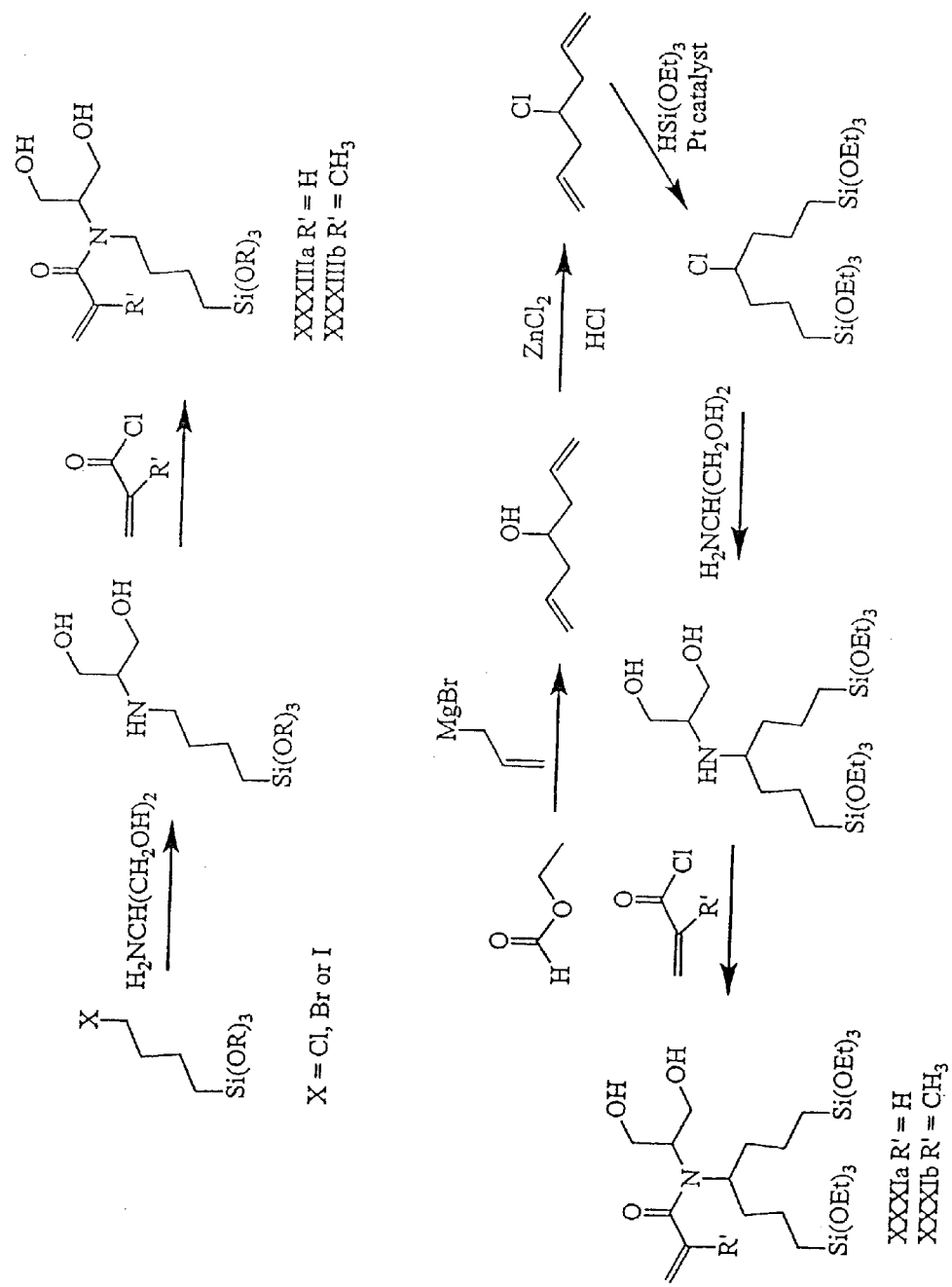
FIG. 28 is a scheme showing the synthesis of silicon compounds XXXIa–b and XXXIIIa–b.

FIG. 28 provides an exemplary reaction scheme for compounds of Formula 18, for example, structures XXXI*a* and XXXI*b*. Preparation begins with the formation of 1,6-heptadiene-4-ol from reaction of ethyl formate with allylmagnesium bromide (Aldrich, Milwaukee, Wis.). Reaction of the alcohol with zinc chloride by the method of Reeve, W., *J. Org. Chem.* 1969,34, 1921 affords a halo diene which after hydrosilylation can be used to alkylate dihydroxyethylamine (Aldrich, Milwaukee, Wis.). N-acylation with acroyl chloride (XXXI*a*) or methacroyl chloride (XXXI*b*) (Aldrich, Milwaukee, Wis.) following the procedure of Yokota, M., et al., European patent Application 97309882.5, 1998 affords the desired compounds.

Figure 29:
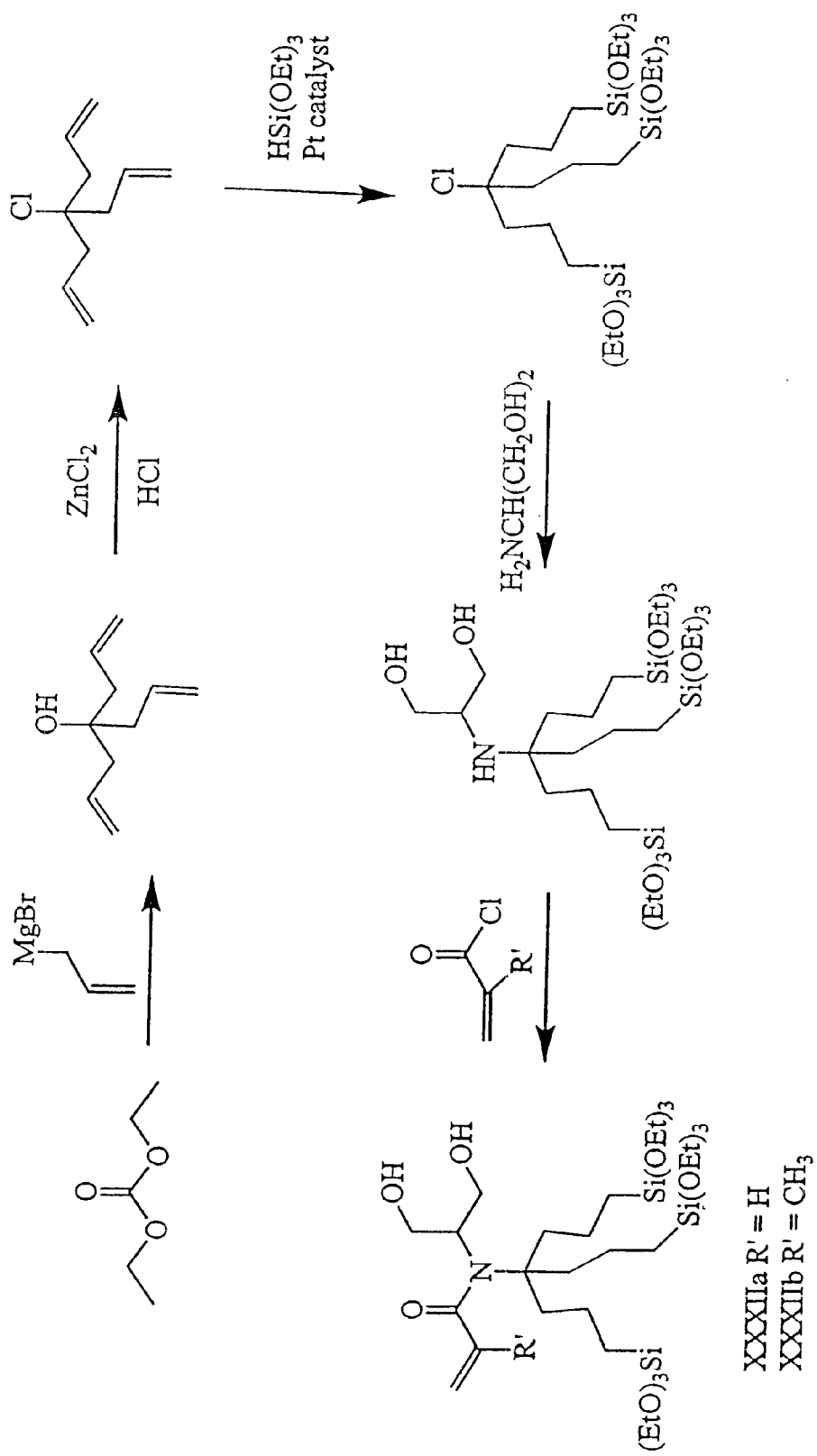
FIG. 29 is a scheme showing the synthesis of silicon compounds XXXIIa–b.

FIG. 29 provides an exemplary reaction scheme for compounds of Formula 20, including structures XXXII*a* and XXXII*b*. Preparation begins with the formation of triallylmethanol from reaction of diethyl carbonate with allylmagnesium bromide by the method of Dreyfuss, M. P., *J. Org. Chem.* 1963,28, 3269. Reaction of the alcohol with zinc chloride by the method of Reeve, W., *J. Org. Chem.* 1969, 34, 192 affords a halo diene which after hydrosilylation can be used to alkylate dihydroxyethylamine (Aldrich, Milwaukee, Wis.). N-acylation with acroyl chloride (XXXI*a*) or methacroyl chloride (XXXI*b*) (Aldrich, Milwaukee, Wis.) following the procedure of Yokota, M.; et al., European patent Application 97309882.5, 1998 affords the desired compounds.

FIG. 28 provides an exemplary reaction scheme for structures XXXIII*a* and XXXIII*b*, compounds which contain a single silicon atom. Preparation begins with the alkylation of dihydroxyethylamine (Aldrich, Milwaukee, Wis.) with an appropriate 3-halo-1-trialkoxylsilylproane reagent, followed by N-acylation with acroyl chloride (XXXIII*a*) or methacroyl chloride (XXXIII*b*) (Aldrich, Milwaukee, Wis.) following the procedure of Yokota, M., et al., European patent Application 97309882.5, 1998 affords the desired compounds.

Functionalized silicon compounds within the scope of the invention that may be used to form functionalized covalent coatings on surfaces that are useful in a variety of applications and assays further include amine compounds such as compound XI, as well as reaction products formed therefrom as disclosed herein.

Applications

The methods and compositions disclosed herein may be used in a variety of applications. The functionalized silicon compounds may be covalently attached to a variety of materials, to provide derivatizable functional groups on the materials. Exemplary materials include materials that comprise a functional group that is capable of reacting with the activated silicon group of the silicon compound. For example, the material may comprise a silica material comprising surface silanols capable of reacting with the activated silicon group to form a siloxane bond between the silicon atom on the silicon compound and the silicon atom on the surface. Thus, the functionalized silicon compounds may be attached to, for example, materials comprising silica, such as glass, chromatography material, and solid supports used for solid phase synthesis, such as nucleic acid synthesis. The functionalized silicon compounds further may be attached to materials comprising oxides such as titanium(IV) dioxide and zirconium dioxide, aluminum oxide and indium-tin oxides, as well as nitrides, such as silicon nitride.

Solid substrates which may be coated by the silicon compounds include any of a variety of fixed organizational support matrices. In some embodiments, the substrate is substantially planar. In some embodiments, the substrate may be physically separated into regions, for example, with trenches, grooves, wells and the like. Examples of substrates include slides, beads and solid chips. The solid substrates may be, for example, biological, nonbiological, organic, inorganic, or a combination thereof, and may be in forms including particles, strands, gels, sheets, tubing, spheres, containers, capillaries, pads, slices, films, plates, and slides depending upon the intended use.

The functionalized silicon compounds used advantageously may be selected with selected properties for a particular application. Functionalized silicon compounds may be selected which can form silicon compound surface coatings that have good stability to hydrolysis. Functionalized silicon compounds may be selected which have a selected reactivity with the substrate and a selected derivatizable functional group depending on the intended use.

In one embodiment, the functionalized silicon compounds may be covalently attached to the surface of a solid substrate to provide a coating comprising derivatizable functional groups on the substrate, thus permitting arrays of immobilized oligomers to be covalently attached to the substrate via covalent reaction with the derivatizable functional groups. The immobilized oligomers, such as polypeptides, or nucleic acids can be used in a variety of binding assays including biological binding assays. In one embodiment, high density arrays of immobilized nucleic acid probes may be formed on the substrate, and then one or more target nucleic acids comprising different target sequences may be screened for binding to the high density array of nucleic acid probes comprising a diversity of different potentially complementary probe sequences. For example, methods for light-directed synthesis of DNA arrays on glass substrates is described in McGall et al., *J. Am. Chem. Soc.,* 119:5081–5090 (1997), the disclosure of which is incorporated herein.

Silanation of glass substrates with the silicon compounds described herein can be conducted, for example by dip-, or spin-application with a 1% –10% solution of silicon compound in an aqueous or organic solvent or mixture thereof, for example in 95% EtOH, followed by thermal curing. See, for example, Arkles, *Chemtech,* 7:766–778 (1997); Leyden, Ed., "Silanes Surfaces and Interfaces, Chemically Modified Surfaces," Vol. 1, Gordon & Breach Science, 1986; and Plueddemann, E. P., Ed., "Silane Coupling Reagents", Plenum Pub. Corp., 1991, the disclosures of which are incorporated herein. Methods for screening target molecules for specific binding to arrays of polymers, such as nucleic acids, immobilized on a solid substrate, are disclosed, for example, in U.S. Pat. No. 5,510,270, the disclosure of which is incorporated herein. The fabrication of arrays of polymers, such as nucleic acids, on a solid substrate, and methods of use of the arrays in different assays, are also described in: U.S. Pat. Nos. 5,677,195, 5,624,711, 5,599,695, 5,445,934, 5,451,683, 5,424,186, 5,412,087, 5,405,783, 5,384,261, 5,252,743 and 5,143,854; PCT WO 92/10092; and U.S. application Ser. No. 08/388,321, filed Feb. 14, 1995, the disclosures of each of which are incorporated herein. Accessing genetic information using high density DNA arrays is further described in Chee, *Science* 274:610–614 (1996), the disclosure of which is incorporated herein by reference. The combination of photolithographic and fabrication techniques allows each probe sequence to occupy a very small site on the support. The site may be as small as a few microns or even a small molecule. Such probe arrays may be of the type known as Very Large Scale Immobilized Polymer Synthesis (VLSIPS®) arrays, as described in U.S. Pat. No. 5,631,734, the disclosure of which is incorporated herein.

In the embodiment wherein solid phase chemistry, photolabile protecting groups and photolithography are used to create light directed spatially addressable parallel chemical synthesis of a large array of polynucleotides on the substrate, as described in U.S. Pat. No. 5,527,681, the disclosure of which is incorporated herein, computer tools may be used for forming arrays. For example, a computer system may be used to select nucleic acid or other polymer probes on the substrate, and design the layout of the array as described in U.S. Pat. No. 5,571,639, the disclosure of which is incorporated herein.

Substrates having a surface to which arrays of polynucleotides are attached are referred to herein as "biological chips". The substrate may be, for example, silicon or glass, and can have the thickness of a microscope slide or glass cover slip. Substrates that are transparent to light are useful when the assay involves optical detection, as described, e.g., in U.S. Pat. No. 5,545,531, the disclosure of which is incorporated herein. Other substrates include Langmuir Blodgett film, germanium, (poly)tetrafluoroethylene, polystyrene, (poly)vinylidenedifluoride, polycarbonate, gallium arsenide, gallium phosphide, silicon oxide, silicon nitride, and combinations thereof. In one embodiment, the substrate is a flat glass or single crystal silicon surface with relief features less than about 10 Angstoms.

The surfaces on the solid substrates will usually, but not always, be composed of the same material as the substrate. Thus, the surface may comprise any number of materials, including polymers, plastics, resins, polysaccharides, silica or silica based materials, carbon, metals, inorganic glasses, membranes, or any of the above-listed substrate materials. Preferably, the surface will contain reactive groups, such as carboxyl, amino, and hydroxyl. In one embodiment, the surface is optically transparent and will have surface Si—OH functionalities such as are found on silica surfaces.

In the embodiment wherein arrays of nucleic acids are immobilized on a surface, the number of nucleic acid sequences may be selected for different applications, and may be, for example, about 100 or more, or, e.g., in some embodiments, more than $10^5$ or $10^8$. In one embodiment, the surface comprises at least 100 probe nucleic acids each preferably having a different sequence, each probe contained in an area of less than about 0.1 $cm^2$, or, for example, between about 1 $\mu m^2$ and 10,000 $\mu m^2$, and each probe nucleic acid having a defined sequence and location on the surface. In one embodiment, at least 1,000 different nucleic acids are provided on the surface, wherein each nucleic acid is contained within an area less than about $10^{-3}$ $cm^2$, as described, for example, in U.S. Pat. No. 5,510,270, the disclosure of which is incorporated herein.

Arrays of nucleic acids for use in gene expression monitoring are described in PCT WO 97/10365, the disclosure of which is incorporated herein. In one embodiment, arrays of nucleic acid probes are immobilized on a surface, wherein the array comprises more than 100 different nucleic acids and wherein each different nucleic acid is localized in a predetermined area of the surface, and the density of the different nucleic acids is greater than about 60 different nucleic acids per 1 $cm^2$.

Arrays of nucleic acids immobilized on a surface which may be used also are described in detail in U.S. Pat. No. 5,744,305, the disclosure of which is incorporated herein. As disclosed therein, on a substrate, nucleic acids with different sequences are immobilized each in a predefined area on a surface. For example, 10, 50, 60, 100, $10^3$, $10^4$, $10^5$, $10^6$, $10^7$, or $10^8$ different monomer sequences may be provided on the substrate. The nucleic acids of a particular sequence are provided within a predefined region of a substrate, having a surface area, for example, of about 1 $cm^2$ to $10^{-10}$ $cm^2$. In some embodiments, the regions have areas of less than about $10^{-1}$, $10^{-2}$, $10^{-3}$, $10^{-4}$, $10^{-5}$, $10^{-6}$, $10^{-7}$, $10^{-8}$, $10^{-9}$, or $10^{-10}$ $cm^2$. For example, in one embodiment, there is provided a planar, non-porous support having at least a first surface, and a plurality of different nucleic acids attached to the first surface at a density exceeding about 400 different nucleic acids/$cm^2$, wherein each of the different nucleic acids is attached to the surface of the solid support in a different predefined region, has a different determinable sequence, and is, for example, at least 4 nucleotides in length. The nucleic acids may be, for example, about 4 to 20 nucleotides in length. The number of different nucleic acids may be, for example, 1000 or more. In the embodiment where polynucleotides of a known chemical sequence are synthesized at known locations on a substrate, and binding of a complementary nucleotide is detected, and wherein a fluorescent label is detected, detection may be implemented by directing light to relatively small and precisely known locations on the substrate. For example, the substrate is placed in a microscope detection apparatus for identification of locations where binding takes place. The microscope detection apparatus includes a monochromatic or polychromatic light source for directing light at the substrate, means for detecting fluoresced light from the substrate, and means for determining a location of the fluoresced light. The means for detecting light fluoresced on the substrate may in some embodiments include a photon counter. The means for determining a location of the fluoresced light may include an x/y translation table for the substrate. Translation of the substrate and data collection are recorded and managed by an appropriately programmed digital computer, as described in U.S. Pat. No. 5,510,270, the disclosure of which is incorporated herein.

Devices for concurrently processing multiple biological chip assays may be used as described in U.S. Pat. No. 5,545,531, the disclosure of which is incorporated herein. Methods and systems for detecting a labeled marker on a sample on a solid support, wherein the labeled material emits radiation at a wavelength that is different from the excitation wavelength, which radiation is collected by collection optics and imaged onto a detector which generates an image of the sample, are disclosed in U.S. Pat. No. 5,578,832, the disclosure of which is incorporated herein. These methods permit a highly sensitive and resolved image to be obtained at high speed. Methods and apparatus for detection of fluorescently labeled materials are further described in U.S. Pat. Nos. 5,631,734 and 5,324,633, the disclosures of which are incorporated herein.

The methods and compositions described herein may be used in a range of applications including biomedical and genetic research and clinical diagnostics. Arrays of polymers such as nucleic acids may be screened for specific binding to a target, such as a complementary nucleotide, for example, in screening studies for determination of binding affinity and in diagnostic assays. In one embodiment, sequencing of polynucleotides can be conducted, as disclosed in U.S. Pat. No. 5,547,839, the disclosure of which is incorporated herein. The nucleic acid arrays may be used in many other applications including detection of genetic diseases such as cystic fibrosis, diabetes, and acquired diseases such as cancer, as disclosed in U.S. patent application Ser. No. 08/143,312, the disclosure of which is incorporated herein. Genetic mutations may be detected by sequencing by hybridization. In one embodiment, genetic markers may be sequenced and mapped using Type-IIs restriction endonucleases as disclosed in U.S. Pat. No. 5,710,000, the disclosure of which is incorporated herein.

Other applications include chip based genotyping, species identification and phenotypic characterization, as described in U.S. patent application Ser. No. 08/797,812, filed Feb. 7, 1997, and U.S. application Ser. No. 08/629,031, filed Apr. 8, 1996, the disclosures of which are incorporated herein.

Gene expression may be monitored by hybridization of large numbers of mRNAs in parallel using high density arrays of nucleic acids in cells, such as in microorganisms such as yeast, as described in Lockhart et al., *Nature Biotechnology*, 14:1675–1680 (1996), the disclosure of which is incorporated herein. Bacterial transcript imaging by hybridization of total RNA to nucleic acid arrays may be conducted as described in Saizieu et al., *Nature Biotechnology*, 16:45–48 (1998), the disclosure of which is incorporated herein.

All publications cited herein are incorporated herein by reference in their entirety.

The invention will be further understood by the following non-limiting examples.

EXAMPLES

Example 1

Silicon compounds were obtained commercially or synthesized from commercially available starting materials. Silicon compounds N,N-bis(2-hydroxyethyl)-3-aminopropyltriethoxysilane, and N-(2-hydroxyethyl)-N-methyl-3-aminopropyltriethoxysilane (compound I) were purchased from Gelest, Inc (Tullytown, Pa.).

Silicon compounds II and V and were prepared as shown in Schemes II and III. Solutions of the starting materials, bis(trimethoxysilyl-propyl)amine and bis[(3-trimethoxysilyl)propyl]ethylenediamine in methanol (62 wt %, from Gelest, Inc.) were combined with 1.1–2.2 theoretical equivalents of ethylene oxide at room temperature under a dry ice-acetone condenser. The resulting solutions were analyzed by $^1$H—NMR, which indicated 95% conversion in some runs to the hydroxyethylated products, and these were used without further purification. In other runs, a 60–65% conversion was obtained for compound V and also was used without further purification.

$^1$H—NMR(CDCl$_3$) data are provided below:

(II): 0.55–0.70 (br m, 4H), 1.55–1.65 (br m, 4H), 2.40–2.50 (br m, 2H), 2.55–2.60 (br m, 4H), 3.50 (s, MeOH), 3.55 (d, 9H), 3.75 (t, 2H);

(V): 0.55–0.70 (br m, 4H), 1.50–1.65 (br m, 4H), 2.40–2.80 (br m, 12H), 3.50 (s, MeOH), 3.40–3.60 (m–s, ~20H), 3.75 (m, ~3–4H);

Substrates were treated by a silanation procedure as follows. Glass substrates (borosilicate float glass, soda lime or fused silica, 2"×3"×0.027", obtained from U.S. Precision Glass (Santa Rosa, Calif.) were cleaned by soaking successively in Nanostrip (Cyantek, Fremont, Calif.) for 15 minutes, 10% aqueous NaOH/70° C. for 3 minutes, and then 1% aqueous HCl for 1 minute (rinsing thoroughly with deionized water after each step). Substrates were then spin-dried for 5 minutes under a stream of nitrogen at 35° C. Silanation was carried out by soaking under gentle agitation in a freshly prepared 1–2% (wt/vol) solution of the silicon compound in 95:5 ethanol-water for 15 minutes. The substrates were rinsed thoroughly with 2-propanol, then deionized water, and finally spin-dried for 5 minutes at 90°–110° C.

The stability of silicon compound bonded phase was evaluated. The surface hydroxyalkylsilane sites on the resulting substrates were "stained" with fluorescein in a checkerboard pattern by first coupling a MeNPOC—HEG linker phosphoramidite, image-wise photolysis of the surface, then coupling to the photo-deprotected linker sites a 1:20 mixture of fluorescein phosphoramidite and DMT—T phosphoramidite (Amersham-Pharmacia Biotech, Piscataway, N.J.), and then deprotecting the surface molecules in 1:1 ethylenediamine-ethanol for 4 hr. The steps were conducted using standard protocols, as described in McGall et al., *J. Am. Chem. Soc.*, 119:5081–5090 (1997), the disclosure of which is incorporated herein.

The pattern and intensity of surface fluorescence was imaged with a scanning laser confocal fluorescence microscope, which employed excitation with a 488 nm argon ion laser beam focused to a 2 micron spot size at the substrate surface. Emitted light was collected through confocal optics with a 530(+15) nm bandpass filter and detected with a PMT equipped with photon counting electronics. Output intensity values (photon counts/second) are proportional to the amount of surface-bound fluorescein, so that relative yields of free hydroxyl groups within different regions of the substrate could be determined by direct comparison of the observed surface fluorescence intensities. All intensity values were corrected for nonspecific background fluorescence, taken as the surface fluorescence within the non-illuminated regions of the substrate.

The relative surface reactive site density was measured. For each silicon compound tested, the number of available surface synthesis sites achieved per unit area was estimated, relative to N,N-bis(2-hydroxyethyl)-3-aminopropyltriethoxysilane, by comparison of the observed initial surface fluorescence intensities of the various substrates immediately after deprotection in ethanolic diaminoethane.

$$\text{Site Density}(\% \text{ rel.}) = \frac{\text{Intensity(silicon compound ``}X\text{'')} \times 100}{\text{Intensity (silicon compound II)}}$$

To determine the relative stability of the silicon compound coatings, substrates were gently agitated on a rotary shaker at 45° C. in 5xSSPE or 6xSSPE aqueous buffer (BioWhittacker Products, Walkersville, Md.) at pH 7.3. Periodically, the substrates were removed from the buffer and re-scanned to measure the amount of fluorescein remaining bound to the surface.

Figure 11:
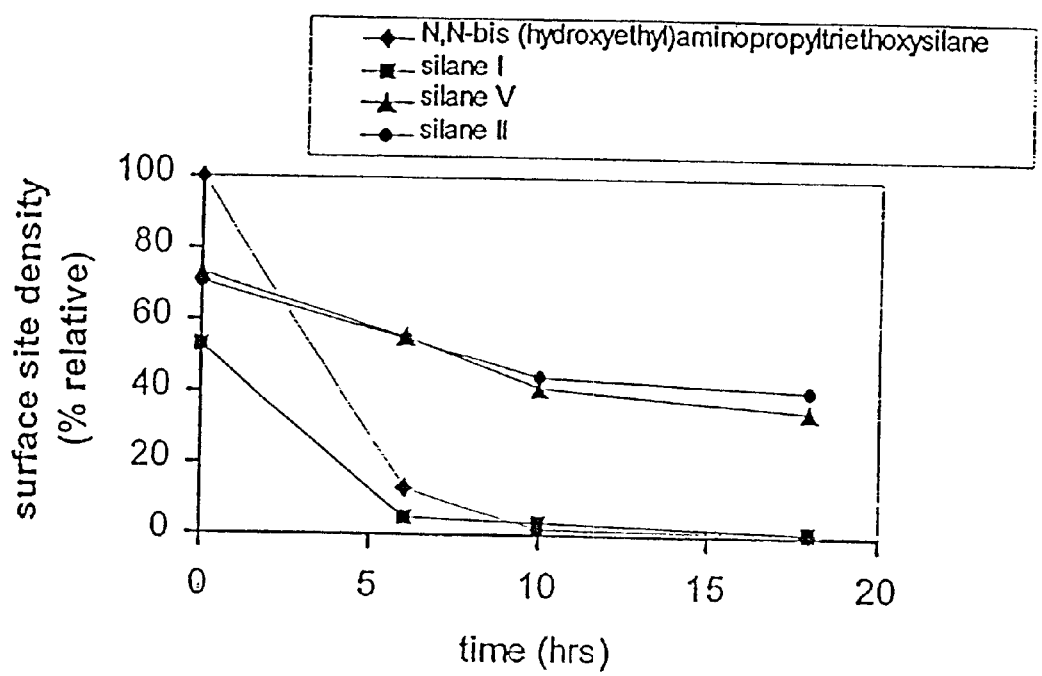
FIG. 11 is a graph of stability of silicon compound bonded phases vs. time.

The results are shown in FIG. 11. As shown in FIG. 11, more of the fluorescein tag remained bound to the substrate after prolonged exposure to the aqueous buffer in the case of substrates silanated with II or V, than remained bound to the substrates silanated with N,N-bis(2-hydroxyethyl)-3-aminopropyltriethoxysilane or compound I. This demonstrates that the surface bonded phase obtained with silicon compounds II or V is much more stable towards hydrolysis than that obtained with N,N-bis(2-hydroxyethyl)-3-aminopropyltriethoxysilane.

Figure 12:
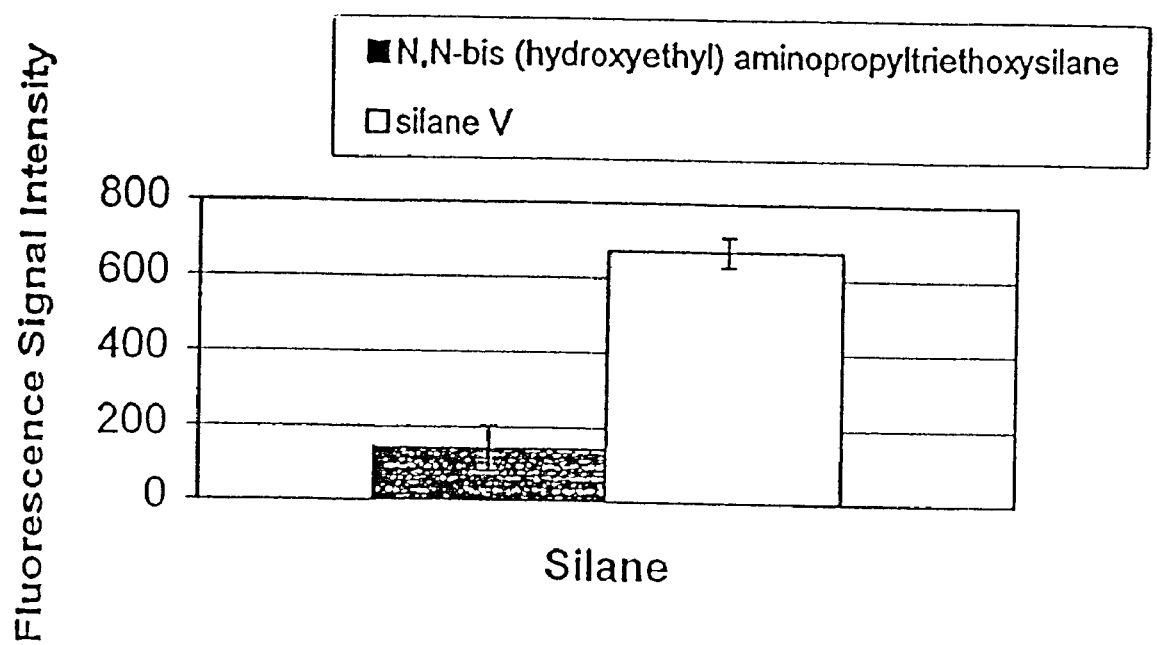
FIG. 12 is a graph of hybridization fluorescence intensity vs. silane.

The hybridization performance of silanated substrates was evaluated. A comparison was made between substrates silanated with N,N-bis(2-hydroxyethyl)-3-aminopropyltriethoxysilane and compound V in terms of performance under typical hybridization assay conditions. A nucleic acid probe sequence (5'-GTC AAG ATG CTA CCG TTC AG-3') (SEQ. ID NO. 1) was synthesized photolithographically in a checkerboard array pattern (400×400 micron features) on the substrates that had been derivatized with either N,N-bis(2-hydroxyethyl)-3-aminopropyltriethoxysilane or silicon compound V. After deprotection in ethanolic diaminoethane, the arrays were hybridized with a fluorescein-labeled complementary "target" nucleic acid (5'-fluorescein-CTG AAC GGT AGC ATC TTG AC-3') (SEQ. ID NO. 2) at a concentration of 250 pM in 6xSSPE buffer (0.9 M NaCl, 60 mM NaH$_2$PO$_4$, 6 mM EDTA, pH 7.5) for 16 hours at 45° C. After cooling to room temperature, the target nucleic acid solution was removed, and the array was washed briefly with 6x SSPE buffer and then scanned on a confocal imaging system. The relative amount of bound target was determined from the fluorescence signal intensity. The hybridization signal intensities obtained with the more stable substrates, derivatized with silicon compound V, were at least four times higher than those obtained with substrates that were derivatized with N,N-bis(2-hydroxyethyl)-3-aminopropyltriethoxysilane. A graph of fluorescence signal intensity vs. silane is shown in FIG. 12.

Example 2

Silicon compound XVI*b* was prepared as shown in FIG. 13. An oven dried 25 ml single-neck flask was charged with 1.07 g (1 ml, 0.0066 mol) N,N-bis(2-hydroxyethyl)-1,3-diaminopropane (TCI America, Portland, Oreg.) and 5 ml anhydrous methanol (Aldrich Chemical; Milwaukee, Wis.). To this stirring solution was added 2.92 ml (3.12 g, 0.0132 mol) (3-glycidoxypropyl)trimethoxysilane (Gelest, Inc., Tullytown, Pa.) dropwise over a 30 minute period. The solution was allowed to stir under an Ar atmosphere until $^1$H NMR indicated that the triplet signal for the (CH$_2$)CH$_2$ (NH$_2$) protons of the starting amine ($\delta$=2.86 ppm) had shifted completely away (41 hours). Molecular ions corresponding to the starting materials were absent in the mass spectrum (positive ion mode) which was dominated by the [M+H]$^+$ peak of m/z=635.5.

Example 3

An alternate preparation of silicon compound XVI*b* was conducted as shown in FIG. 13. An oven dried 25 ml single-neck flask was charged with 1.07 g (1 ml, 0.0066 mol) N,N-bis(2-hydroxyethyl)-1,3-diaminopropane (TCI America, Portland, Oreg.) and 5 ml anhydrous methanol (Aldrich Chemical; Milwaukee, Wis.). To this stirring solution was added 2.92 ml (3.12 g, 0.0132 mol) (3-glycidoxypropyl)trimethoxysilane (Gelest, Inc., Tullytown, Pa.) dropwise over a 30 minute period. The solution was brought to reflux and allowed to stir under an Ar atmosphere until $^1$H NMR indicated that the triplet signal for the (CH$_2$)CH$_2$(NH$_2$) protons of the starting amine ($\delta$=2.86 ppm) had shifted completely away (17 hours).

Molecular ions corresponding to the starting materials were absent in the mass spectrum (positive ion mode), an M+H$^+$ peak of m/z=635.5 was observed but it did not dominate the spectrum as seen in the room temperature preparation of Example 2.

Example 4

Silicon compound XVI*e* was prepared as shown in FIG. 13. An oven dried 25 ml single-neck flask was charged with 2.74 g (0.026 mol) tris(hydroxymethyl)-methylamine (Aldrich Chemical; Milwaukee, Wis.), 10 ml (10.70 g, 0.0452 mol) (3-glycidoxypropyl)trimethoxysilane (Gelest, Inc., Tullytown, Pa.), and 11 ml anhydrous methanol (Aldrich Chemical; Milwaukee, Wis.). The suspension was allowed to stir under an Ar atmosphere. After all the solids dissolved (6 days), $^{13}$C NMR indicated that the singlet signal for the C(CH$_2$OH)$_3$ carbon of the starting amine ($\delta$=55.38 ppm) had shifted completely away. $^{13}$C NMR ($\delta$, ppm): 73.12 (CH—OH), 71.03 (C—N), 61.94 (CH$_2$OH), 50.62 (C—[OC]), 50.06 ([C]—C—O), 49.39 (CH$_3$OSi), 43.85 (N—C—[CH$_2$OH]$_3$), 22.34 (C—[CSi]), 4.81 (C—Si). Mass Spectrum: M$^+$ (m/z 593.4) and [M—CH$_3$OH]$^+$ (m/z 561.5).

Example 5

A solution of 104 g triphosgene (0.102 mol) (Aldrich Chemical; Milwaukee, Wis.) and 1 liter anhydrous THF (Aldrich Chemical; Milwaukee, Wis.) was prepared under Ar in a 2–1 oven-dried flask. To the stirring solution was slowly added 42.5 ml (30.8 g, 0.304 mol) triethylamine (Aldrich Chemical; Milwaukee, Wis.) and a white precipitate formed. The stirring suspension was cooled in ice and 100 ml N,N-bis(3-trimethoxysilylpropyl)amine (104 g, 0.304 mol) (compound XIV, Gelest, Inc., Tullytown, Pa.) was added dropwise over an hour. The reaction mixture was allowed to stir for 21.5 hours then filtered under an Ar blanket and the solids washed with anhydrous THF. The filtrate was concentrated under reduced pressure to an orange oil and dried under vacuum to give 116 g of product (95% crude yield). $^1$H NMR ($\delta$, ppm): 3.57 (s, CH$_3$OSi), 3.32 (dd, CH$_2$—NC=O, 4 H), 1.70 (q, [CH$_2$]—CH$_2$—[CH$_2$], 4 H), 0.58 (t, CH$_2$Si, 4 H). $^{13}$C NMR ($\delta$, ppm): 149.14 (C=O), 53.53 (C—N—C=O), 52.25 (C—N—C=O), 50.66 (CH$_3$OSi), 21.83 (C—C—N), 20.82 (C—C—N), 6.50 (C—Si).

Example 6

Silicon compound XVII*b* was prepared as shown in FIG. 14. An oven dried 25 ml single-neck flask was charged with 0.21 ml (0.15 g, 0.0015 mol) triethylamine (Aldrich Chemical; Milwaukee, Wis.), 0.61 g of a carbamoyl chloride prepared as per Example 5 (0.0015 mol), and 5 ml anhydrous THF (Aldrich Chemical; Milwaukee, Wis.). After addition of 0.20 g (0.0015 mol) diethanolamine (Aldrich Chemical; Milwaukee, Wis.) a precipitate formed. After 5 days of stirring under Ar at room temperature, the mixture was filtered and concentrated to a brown oil. After drying under vacuum, 0.62 g (87% crude yield) of material was obtained. The oil was dissolved in 0.6 ml methanol and stored. $^{13}$C NMR (δ, ppm): 166.29 (C=O), 60.50 (C—OH), 57.28 (N—C—COH), 46.14 (C—C—N), 21.01 (C—[CSi]), 6.27 (C—Si). Mass Spectrum: [M+H]$^+$ (m/z 473) and [M—CH$_3$O]$^+$ (m/z 441).

Example 7

Silicon compound XVII$f$ was prepared as shown in FIG. 14. An oven dried 25 ml single-neck flask was charged with 42.4 ml (30.8 g, 0.304 mol) triethylamine (Aldrich Chemical; Milwaukee, Wis.), 116 g of a carbamoyl chloride prepared as per Example 5 (0.304 mol), and 500 ml anhydrous THF (Aldrich Chemical; Milwaukee, Wis.). After addition of 1.07 g (1 ml, 0.0066 mol) N,N-Bis(2-hydroxyethyl)-1,3-diaminopropane (TCI America, Portland, Oreg.), 500 ml anhydrous CH$_2$Cl$_2$ (Aldrich Chemical; Milwaukee, Wis.) was added. The mixture was stirred under Ar at room temperature, during which time an insoluble orange oil formed. After 18 hours, $^1$H NMR indicated that the triplet signal for the (CH$_2$)CH$_2$(NH$_2$) protons of the starting amine (δ=2.86 ppm) had shifted completely away. The mixture was decanted and the filtrate concentrated. The concentrate was combined with 400 ml anhydrous THF (Aldrich Chemical; Milwaukee, Wis.). The resultant suspension was filtered, concentrated under reduced pressure, and dried under vacuum to yield 145 g (95% crude yield) of a faint orange oil. The oil was dissolved in 150 ml methanol and stored. Mass Spectrum: [M+H]$^+$ (m/z 530).

Example 8

Coated substrates with XVI$b$, XVI$e$, XVII$b$, and XVII$f$ were prepared by a modified version of the silanation procedure of Example 1. In this case, the silane content of the 95:5 ethanol:water bath was 1–2% by volume of the methanol/silane compound solutions described in Examples 2–4 and 6–7 and curing was done at 50° C. for 2 minutes.

Example 9

Evaluation of stability of the silicon bonded phase, relative surface reactive site density, and hybridization performance of substrates coated with XVI$b$, XVI$e$, XVII$b$, and XVII$f$ was carried out in a single experimental protocol. First, MeNPOC—HEG linker phosphoramidite is coupled to the surface, then image-wise photolysis is used to pattern the surface into a series of stripes. Two stripes, 400 μm×12800 μm, were stained with fluorescein label to evaluate stability of the silicon bonded phase and relative surface reactive site density. A nucleic acid probe sequence was synthesized-photolithographically into two additional stripes, 1600 μm×12800 μm. After patterning, the surface is deprotected in 1:1 ethylenediamine ethanol for 4 hours. The steps were conducted using standard protocols, as described in McGall et al., *J. Am. Chem. Soc.*, 119:5081–5090 (1997), the disclosure of which is incorporated herein. The pattern and intensity of surface fluorescence from both fluorescein labeled patterns and adsorbed fluorescein labeled target oligonucleotide is imaged with a scanning fluorescence microscope as described in Example 1.

Figure 30:
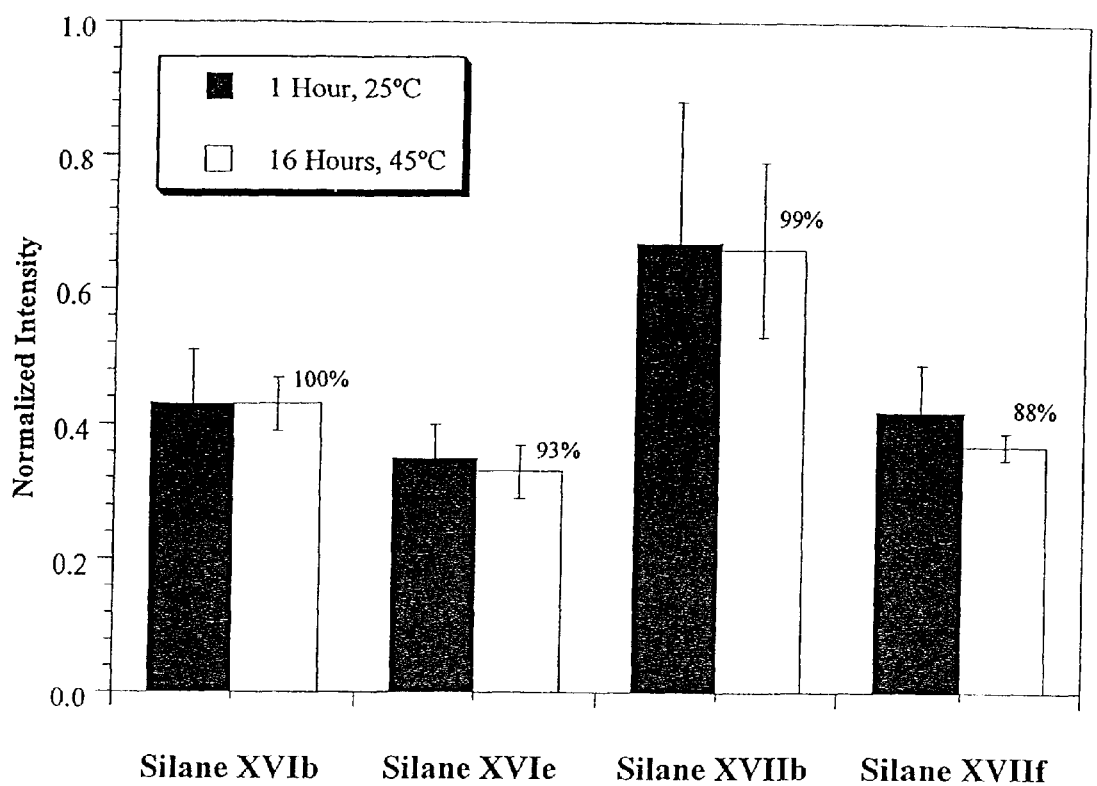
FIG. 30 is a graph of normalized intensity vs. silane for silicon compounds bound to a solid substrate.

In the assay the surface was imaged after a period of 1 hour exposure to 5 nM target in 6X SSPE buffer (0.9 M NaCl, 60 mM NaH$_2$PO$_4$, 6 mM EDTA, pH 7.5) at 25° C. and again after 16 hours at 45° C. Except as noted herein, the method employed for the assay is the same as described in Example 1. The fluorescence intensity was averaged and evaluated at both the 1 hour and 16 hour time points. Relative surface reactive site density was determined by normalization of the signal to that obtained from compound I as described in Example 1. FIG. 30 shows the normalized data at the 1 and 16 hour time points. The percentage of remaining fluorescence intensity is noted for the 16-hour time point for each silane coating.

Figure 31:
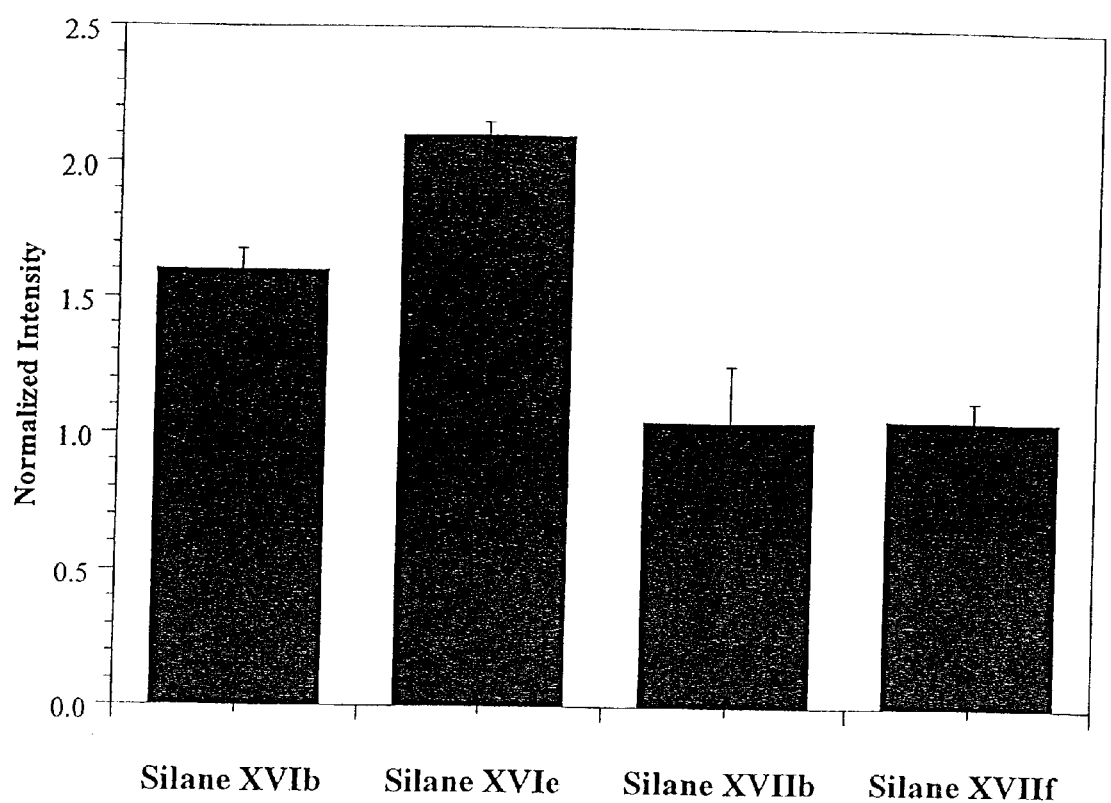
FIG. 31 is a graph of normalized hybridization fluorescence intensity vs. silane.

Hybridization performance of substrates for matched probes is illustrated in FIG. 31, where the 1 hour, 25° C. intensities of the averaged background corrected fluorescence signals of the matched sequence stripes are shown. Signals are normalized to 1=intensity of identical probes synthesized on N,N-bis(2-hydroxyethyl)-3-trimethoxypropylamine (compound I) surfaces.

What is claimed is:

1. A method of functionalizing a surface, comprising a covalently attaching to the surface a functionalized silicon compound having a structure of Formula 3:

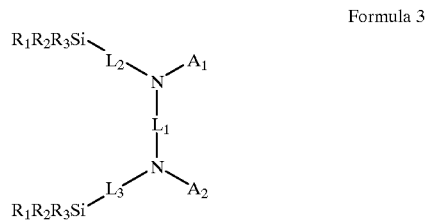

Formula 3 wherein R$_1$ and R$_2$ are independently selected from the group consisting of alkoxy or halide, and R$_3$ is selected from the group consisting of alkoxy, halide and alkyl;

wherein L$_1$, L$_2$, and L$_3$ are independently —(CH$_2$)$_n$—, wherein n is 2–10; and wherein A$_1$ and A$_2$ are independently a moiety comprising one or more derivatizable functional groups or modified forms thereof.

2. The method of claim 1, wherein the method comprises covalently attaching a plurality of functionalized silicon compounds to the surface; and forming an array of nucleic acids covalently attached to the functionalized silicon compounds on the surface.

3. The method of claim 1, wherein the method comprising covalently attaching to the surface a functionalized silicon compound having a structure of Formula 3:

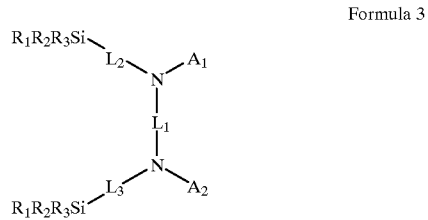

Formula 3 wherein R$_1$ and R$_2$ are independently alkoxy or halide, and R$_3$ is selected from the group consisting of alkoxy, halide and alkyl;

wherein $L_1$, $L_2$, and $L_3$ are independently —$(CH_2)_n$—, wherein n is 2 to 10 ; and wherein $A_1$ and $A_2$ are independently H or a moiety comprising one or more derivatizable functional groups selected from the group consisting of hydroxyl, amino, amido, carboxyl, thio, halo, and sulfonate.

4. The method of claim 3, wherein the one or more derivatizable functional groups are hydroxyl groups, activated hydroxyl groups or protected hydroxyl groups.

5. The method of claim 3, wherein $A_1$ and $A_2$ each comprise a plurality of derivatizable functional groups.

6. A method of functionalizing a surface comprising covalently attaching a functionalized silicon compound to the surface, wherein the silicon compound is a compound having a structure of Formula V:

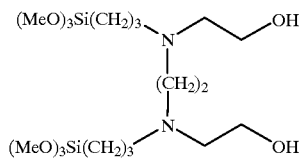

V

7. The method of claim 1, wherein the surface is the surface of a substrate comprising silica.

8. The method of claim 3, wherein the surface is the surface of a substrate comprising silica.

9. The method of claim 1, wherein the substrate is in a form selected from the group consisting of particles, films and chips.

* * * * *